US006362342B1

(12) United States Patent
Qi et al.

(10) Patent No.: US 6,362,342 B1
(45) Date of Patent: Mar. 26, 2002

(54) TRIAZOLE COMPOUNDS AND METHODS OF MAKING SAME

(75) Inventors: Ming Qi, San Diego; R. Normand Hebert, Cardiff by the Sea, both of CA (US); Alan R. Katritzky, Gainsville, FL (US)

(73) Assignee: Lion Bioscience AG (DE)

( * ) Notice: Subject to any disclaimer, the term of this patent is extended or adjusted under 35 U.S.C. 154(b) by 0 days.

(21) Appl. No.: 09/342,987

(22) Filed: Jun. 29, 1999

(51) Int. Cl.$^7$ ............................................ C07D 249/08
(52) U.S. Cl. ................ 548/262.2; 514/383; 540/267.8; 540/269.4
(58) Field of Search ........................ 514/383; 548/269.4

(56) References Cited

U.S. PATENT DOCUMENTS

| | | | |
|---|---|---|---|
| 4,338,453 A | | 7/1982 | Gall .......................... 548/263 |
| 4,512,997 A | * | 4/1985 | Meier et al. ................ 514/383 |
| 4,598,085 A | | 7/1986 | Heeres et al. ............... 514/383 |
| 5,010,175 A | | 4/1991 | Rutter et al. ................ 530/334 |
| 5,098,920 A | | 3/1992 | Reiz .......................... 514/381 |
| 5,281,614 A | | 1/1994 | Ashton et al. .............. 514/359 |
| 5,288,514 A | | 2/1994 | Ellman .......................... 427/2 |
| 5,318,959 A | * | 6/1994 | Ozaki et al. .................. 514/63 |
| 5,324,483 A | | 6/1994 | Cody et al. ................. 422/131 |
| 5,466,705 A | * | 11/1995 | Ozaki et al. ................ 514/383 |
| 5,482,951 A | * | 1/1996 | Ozaki et al. ................ 514/340 |
| 5,506,337 A | | 4/1996 | Summerton et al. ........ 528/391 |
| 5,549,974 A | | 8/1996 | Holmes ....................... 428/403 |
| 5,556,762 A | | 9/1996 | Pinilla et al. .............. 435/7.21 |
| 5,712,171 A | | 1/1998 | Zambias et al. ............ 436/518 |
| 5,756,522 A | | 5/1998 | Tomioka et al. ............ 514/340 |
| 5,856,350 A | * | 1/1999 | Dalton et al. ............... 514/383 |

FOREIGN PATENT DOCUMENTS

| | | |
|---|---|---|
| WO | WO91/08694 | 6/1991 |
| WO | WO91/19735 | 12/1991 |

OTHER PUBLICATIONS

Dooley et al., "An All D-Amino Acid Opioid Peptide with Central Analgesic Activity from a Combinatorial Library," *Science* 266:2019–2022 (1994).

Eichler and Houghten, "Identification of Substrate–Analog Trypsin Inhibitors through the Screening of Synthetic Peptide Combinatorial Libraries," *Biochemistry* 32:11035–11041 (1993).

Francis et al., "Synthesis and Benzodiazepine Binding Activity of a Series of Novel [1,2,4] Triazolo [1,5–c] quinazolin–5 (6H) –ones," *J. Med. Chem.* 34:281–290 (1991).

Gallop et al., "Applications of Combinatorial Technologies to Drug Discovery," *J. Med. Chem.*, 37:1233–1251 (1994).

Goff et al., "Solid–Phase Synthesis of Highly Substituted Peptoid 1 (2H) –Isoquinolinones," *J. Org. Chem.* 60:5748–5749 (1995).

Hanessian and Xie, "Polymer–Bound p–Alkoxybenzyl Trichloracetimidates: Regents for the Protection of Alcohols as Benzyl Ethers on Solid–Phase," *Tetrahedron Letters*, 39:733–736 (1998).

Houghton et al., "Generation and use of synthetic peptide combinatorial libraries for basic research and drug discovery," *Nature* 354:84–86 (1991).

Wilson et al., "Solid–supported syntheses of 3–thio–1,2, 4–triazoles," *Molecular Diversity* 3:95–112 (1998).

\* cited by examiner

*Primary Examiner*—Floyd D. Higel
(74) *Attorney, Agent, or Firm*—Law Offices of David Spolter; David Spolter

(57) ABSTRACT

The present invention relates to novel triazole compounds of the following formula:

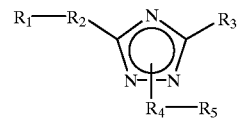

wherein $R_1$ to $R_5$ have the meanings provided herein. The invention further relates to combinatorial libraries containing two or more such compounds, as well as methods of preparing triazole compounds.

12 Claims, 6 Drawing Sheets

X = OH, Cl, Br

TRIAZOLE COMPOUNDS AND METHODS OF MAKING SAME

Background of the Invention

1. Field of the Invention

The present invention relates generally to the synthesis of compounds comprising heterocyclic rings. In one specific embodiment, the invention provides novel triazoles as well as novel combinatorial libraries comprised of such compounds.

2. BACKGROUND INFORMATION

The process of discovering new therapeutically active compounds for a given indication involves the screening of all compounds from available compound collections. From the compounds tested, one or more structures is selected as promising lead. A large number of related analogs are then synthesized in order to develop a structure-activity relationship and select one or more optimal compounds. With traditional "one-at-a-time" synthesis and biological testing of analogs, this optimization process is long and labor intensive. Adding significant numbers of new structures to the compound collections used in the initial screening step of the discovery and optimization process cannot be accomplished with traditional "one-at-a-time" synthesis methods, except over a time frame of years or even decades. Faster methods are needed what allow for the preparation of up to thousands of related compounds in a matter of days or a few weeks. This need is particularly evident when it comes to synthesizing more complex compounds, such as triazoles.

Combinatorial approaches have recently been extended to "organic," or non-peptide, libraries. Zambias et al. (U.S. Pat. No. 5,712,171) describe a method of generating libraries that contain aminimides, oxazolones, sulfonylaminides and phosphonylaminides as the core structure in spatially arranged arrays. Combinatorial chemical methods have been applied to a limited number of heterocyclic compounds, as described, for example, in Wilson et al., *Molecular Diversity*, 3:95–112 (1998); U.S. Pat. Nos. 5,288,514; 5,324,483; and Goff et al., *J. Org. Chem.*, 60:5748–5749 (1995). See also U.S. Pat. Nos. 5,549,974 and 5,506,337. However, the heterocyclic libraries to date contain compounds of limited diversity and complexity.

Substituent limitations have been overcome for mixtures of peptides and peptidomimetics through the use of solid phase techniques versus solution-phase. An important step in the development of solid-phase techniques was the discovery of methods to prepare large numbers of individual compounds simultaneously, as described, for example, by Houghten in U.S. Pat. No. 4,631,211. These solid phase methods, however, have rarely been applied to the syntheses of complex heterocyclic structures. Therefore a need exists to develop more complex "organic" libraries based on heterocyclic medicinal compounds which would need less time and effort in the synthesis and testing required to bring an organic pharmacetical product to fruition. In short, improved methods for generating therapeutically useful heterocyclic compounds, such as triazole derivatives, are desired.

Triazole compounds have been the subject of investigation in a number of different biological areas. For example, triazole derivatives have been proposed as useful: (a) as benzodiazepine receptor agonists (Francis et al., *J. Med. Chem.*, 34:281–290 (1991); (b) in treating cardiovascular disorders (U.S. Pat. No. 5,098,920); (c) as fungicides and plant-growth regulators (U.S. Pat. No. 4,598,085); (d) as insecticides (U.S. Pat. No. 5,756,522) (e) in treating allergies; (f) in treating hypertension (U.S. Pat. No. 4,338,453); and (g) as angiotensin antagonists (U.S. Pat. No. 5,281,614). However, more complex triazole derivatives, especially with substitutions at the 1 and 2 nitrogen positions, have been difficult to attain.

This invention satisfies this need and provides related advantages as well. The present invention overcomes the known limitations to classical serial organic synthesis of triazole derivatives, for example, as well as the shortcomings of combinatorial chemistry related to triazole compounds. The present invention allows for rapid generation of large diverse libraries of complex triazoles as discrete molecules or molecules bound to solid support, such as a resin. The present invention can utilize a readily available pool of building blocks that can be incorporated into the various regions of the molecule. Furthermore, the method of making the present invention allows for the use of building blocks that contain a wide range of diverse functionality. Therefore, building blocks, such as those described above, can provide libraries that consist of large numbers as well as libraries that are extremely diverse with respect to the functionality contained within those libraries. The present invention combines the techniques of solid-phase synthesis of triazoles and the general techniques of synthesis of combinatorial libraries to prepare highly diverse new triazole compounds.

SUMMARY OF THE INVENTION

The present invention relates to novel triazole compounds of the following formula:

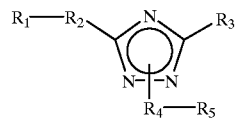

wherein $R_1$ to $R_5$ have the meanings provided below (with $R_4$—$R_5$ attached to either the one-position or two-position nitrogen on the triazole ring).

The invention further relates to combinatorial libraries containing two or more such compounds, and to methods of generating triazole compounds.

BRIEF DESCRIPTION OF THE DRAWINGS

FIG. 1 shows the attachment of hydroxy esters to solid support.

FIG. 2 shows the transformation of resin-bound esters to acyl hydrazines.

FIG. 3 shows triazole ring formation.

FIG. 4 shows reacting resin-bound triazoles with various electrophiles.

FIG. 5 shows the amination of triazole derivatives.

FIG. 6 shows the derivatization of various aminotriazoles.

DETAILED DESCRIPTION OF THE INVENTION

Figure 1:
In FIGS. 1 to 6, described below, $R^1$ corresponds to $R_2$ of the claimed invention; $R^2$ corresponds to $R_3$ of the claimed invention; $R^3$ corresponds to $R_4$ of the claimed invention; $R^4$ corresponds to $R_{16}$ of the claimed invention; and $R^5$ corresponds to $R_{15}$ of the claimed invention.

The present invention provides novel compounds and libraries of novel compounds of the formula:

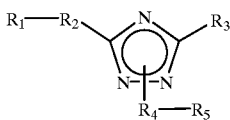

wherein:
- R₁ is —NHC(O)NR₆R₇, —CO₂R₆, —OR₆, —NR₆R₇, —C(O)NR₆R₇, or —CH₂NR₆R₇, wherein R₆ is a hydrogen atom or a functionalized resin, and R₇ is a hydrogen atom, $C_1$ to $C_6$ alkyl, $C_1$ to $C_6$ substituted alkyl, $C_2$ to $C_7$ alkenyl, $C_2$ to $C_7$ substituted alkenyl, phenyl, substituted phenyl, naphthyl, substituted naphthyl, $C_7$ to $C_{12}$ phenylalkyl, $C_7$ to $C_{12}$ substituted phenylalkyl, heteroaryl, substituted heteroaryl, heterocycle or substituted heterocycle;
- R₂ is $C_1$ to $C_{12}$ alkylene, $C_1$ to $C_{12}$ substituted alkylene, $C_2$ to $C_7$ alkenylene, $C_2$ to $C_7$ substituted alkenylene, $C_2$ to $C_7$ alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, phenylene, substituted phenylene, naphthylene, substituted naphthylene, heterocyclene, substituted heterocyclene, heteroarylene, substituted heteroarylene, $C_7$ to $C_{12}$ phenylalkoxy, $C_7$ to $C_{12}$ substituted phenylalkoxy, the formula:

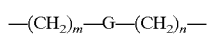

—(CH₂)ₘ—G—(CH₂)ₙ— wherein m and n are integers independently selected from 0 to 6, provided that m and n are not together 0; and G is selected from phenylene and substituted phenylene, the formula:

—(CH₂)ₘ—NX—(CH₂)ₙ— wherein m and n are integers independently selected from 0 to 6, provided that m and n are not together 0; and X is selected from the group consisting of a hydrogen atom, $C_1$ to $C_6$ alkyl, $C_1$ to $C_6$ substituted alkyl, $C_1$ to $C_7$ acyl, $C_1$ to $C_7$ substituted acyl, $C_1$ to $C_4$ alkyl sulfonyl, $C_1$ to $C_4$ substituted alkyl sulfonyl, phenylsulfonyl, substituted phenylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl, substituted phenylaminothiocarbonyl, $C_1$ to $C_7$ alkoxycarbonyl, $C_1$ to $C_7$ substituted alkoxycarbonyl, phenoxycarbonyl or substituted phenoxycarbonyl, the formula:

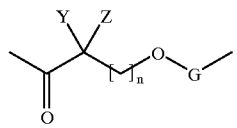

wherein n is an integer selected from 0 to 6; Y and Z are together or independently a hydrogen atom, $C_1$ to $C_6$ alkyl, $C_1$ to $C_6$ substituted alkyl, $C_2$ to $C_7$ alkenyl, $C_2$ to $C_7$ alkynyl, $C_2$ to $C_7$ substituted alkenyl, $C_2$ to $C_7$ substituted alkynyl, $C_1$ to $C_7$ acyl, $C_1$ to $C_7$ substituted acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl or protected hydroxymethyl; and G is phenylene or substituted phenylene, or the formula:

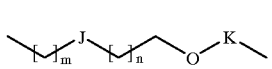

(III)

wherein J and K are each phenylene or substituted phenylene, and m and n are independently 0 or 1;

R₃ is selected from the group consisting of a hydrogen atom, $C_1$ to $C_6$ alkyl, $C_1$ to $C_6$ substituted alkyl, phenyl, substituted phenyl, heteroaryl, substituted heteroaryl, carboxy, protected carboxy, cyano, (monosubstituted) amino, protected (monosubstituted)amino, (disubstituted)amino, $C_1$ to $C_7$ acyl, $C_1$ to $C_7$ substituted acyl, $C_1$ to $C_7$ alkoxycarbonyl, $C_1$ to $C_7$ substituted alkoxycarbonyl, $C_1$ to $C_7$ alkylaminocarbonyl, $C_1$ to $C_7$ substituted alkylaminocarbonyl, phenylaminocarbonyl, substituted phenylaminocarbonyl, heterocycle, substituted heterocycle, naphthyl, substituted naphthyl, $C_5$ to $C_7$ cycloalkyl, $C_5$ to $C_7$ substituted cycloalkyl, $C_5$ to $C_1$ cycloalkenyl and $C_1$ to $C_7$ substituted cycloalkenyl;

R₄ is hydrogen or is selected from the group consisting of the formula:

—D-phenylene-E— wherein:
D is directly attached to the triazole ring and D and E are independently $C_1$ to $C_6$ alkylene, $C_2$ to $C_7$ alkenylene, $C_2$ to $C_7$ alkynylene, $C_1$ to $C_6$ substituted alkylene, $C_2$ to $C_7$ substituted alkenylene, $C_2$ to $C_7$ substituted alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, $C_7$ to $C_{12}$ phenylalkylene, $C_7$ to $C_{12}$ substituted phenylalkylene, —R₁₀—O—R₁₁—, —NR₁₀R₁₁—, —R₁₀—NH—R₁₁— or —C(O)NR₁₀R₁₁—, wherein R₁₀ and R₁₁ are independently absent or present as $C_1$ to $C_6$ alkylene, $C_1$ to $C_6$ substituted alkylene, $C_7$ to $C_{12}$ phenylalkylene or $C_7$ to $C_{12}$ substituted phenylalkylene, provided that, when D is —NR₁₀R₁₁— or —C(O)NR₁₀R₁₁—, R₁₁ is present and directly connected to the triazole ring;

or the formula:

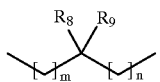

wherein
R₈ and R₉ are together or independently a hydrogen atom, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ acyl, $C_1$ $C_7$ substituted acyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substitute heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino or amino-protecting group; and m and n are independently 0, 1, 2, 3 or 4; and the formulae:

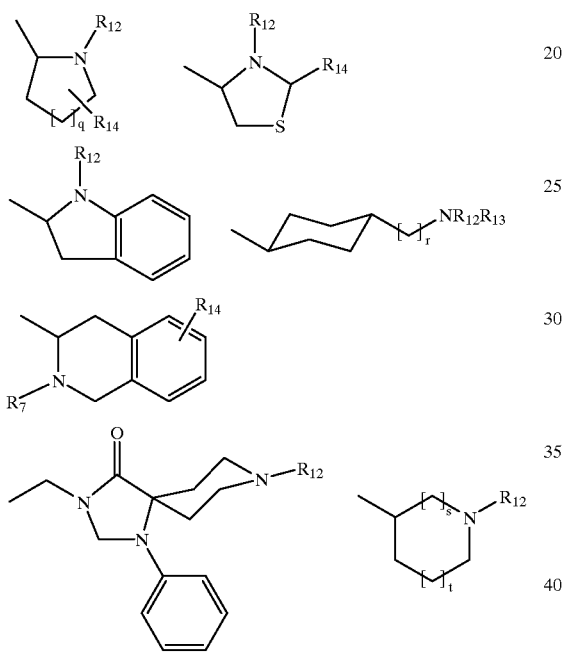

wherein q is 1 or 2; r is 0 or 1; s and t are independently 0, 1 or 2; and $R_{12}$ and $R_{13}$ are independently a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl or substituted phenylaminothiocarbonyl; and $R_{14}$ is a hydrogen atom, —OH, hydroxy-protecting group, $C_1$ to $C_6$ alkyl, $C_1$ to $C_6$ substituted alkyl, $C_1$ to $C_7$ alkoxy, $C_1$ to $C_7$ phenylalkoxy, phenyl, substituted phenyl, heteroaryl or substituted heteroaryl; and $R_5$ is absent or is a hydrogen atom, a halide, —OH, —$CO_2H$, —CHO, —$CO_2R_{15}$, —$C(O)NR_{15}R_{16}$ and —$NR_{15}R_{16}$, wherein $R_{15}$ and $R_{16}$ are independently selected from a hydrogen atom, $C_1$ to $C_6$ alkyl, $C_1$ to $C_6$ substituted alkyl, phenyl, substituted phenyl, heterocycle, substituted heterocycle, heteroaryl, substituted heteroaryl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl, or the formulae:

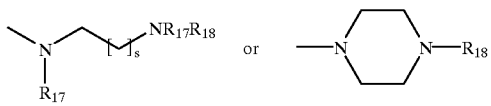

wherein $R_{17}$ and $R_{18}$ are independently a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl or substituted phenylaminothiocarbonyl; and s is 1 to 5.

In one embodiment of the above described compounds and libraries, when (1) $R_8$ and $R_9$ are both hydrogen atoms; or (2) one of $R_8$ and $R_9$ is a hydrogen atom and the other is a $C_1$ to $C_6$ alkyl or $C_1$ to $C_6$ substituted alkyl where the substitution is one or more halides, $R_5$ is not a hydrogen atom or a halide.

In another embodiment of the above described compounds and libraries, when one of $R_8$ and $R_9$ is a hydrogen atom and the other is a $C_2$ to $C_7$ alkenyl, $R_5$ is not a hydrogen atom.

The invention also provides for pharmaceutically acceptable salts of the above-described triazole compounds.

In a preferred embodiment:

$R_1$ is —$NHC(O)NR_6R_7$, —$OR_6$, —$C(O)NR_6R_7$, or —$CH_2NR_6R_7$, wherein $R_6$ is a hydrogen atom or a functionalized resin, and $R_7$ is a hydrogen atom, $C_1$ to $C_6$ alkyl, $C_1$ to $C_6$ substituted alkyl, $C_2$ to $C_7$ alkenyl, $C_2$ to $C_7$ substituted alkenyl, phenyl, substituted phenyl, naphthyl, substituted naphthyl, $C_7$ to $C_{12}$ phenylalkyl, $C_7$ to $C_{12}$ substituted phenylalkyl, heteroaryl, substituted heteroaryl, heterocycle or substituted heterocycle.

In another preferred embodiment:

$R_2$ is $C_1$ to $C_{12}$ alkylene, $C_1$ to $C_{12}$ substituted alkylene, $C_2$ to $C_7$ alkenylene, $C_2$ to $C_7$ substituted alkenylene, $C_2$ to $C_7$ alkynylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, phenylene, substituted phenylene, naphthylene, substituted naphthylene, $C_7$ to $C_{12}$ phenylalkoxy, $C_7$ to $C_{12}$ substituted phenylalkoxy, or
the formula:

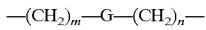

wherein m and n are integers independently selected from 0 to 6, provided that m and n are not together 0; and G is phenylene or substituted phenylene.

In an additional preferred embodiment:

$R_3$ is $C_1$ to $C_6$ alkyl, $C_1$ to $C_6$ substituted alkyl, phenyl, substituted phenyl, heteroaryl, substituted heteroaryl, heterocycle, substituted heterocycle, naphthyl, substituted naphthyl, $C_5$ to $C_7$ cycloalkyl, $C_5$ to $C_7$ substituted cycloalkyl, $C_5$ to $C_7$ cycloalkenyl or $C_5$ to $C_7$ substituted cycloalkenyl.

In another preferred embodiment:

$R_4$ is the formula:

—D-phenylene-E— wherein:

D is directly attached to the triazole ring and D and E are independently $C_1$ to $C_6$ alkylene, $C_2$ to $C_7$ alkenylene, $C_2$ to $C_7$ alkynylene, $C_1$ to $C_6$ substituted alkylene, $C_2$ to $C_7$ substituted alkenylene, $C_2$ to $C_7$ substituted alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, $C_7$ to $C_{12}$ phenylalkylene, $C_7$ to $C_{12}$ substituted phenylalkylene, $—R_{10}—O—R_{11}—$, $—NR_{10}R_{11}—$, $—R_{10}—NH—R_{11}—$ or $—C(O)NR_{10}R_{11}—$, wherein $R_{10}$ and $R_{11}$ are independently absent or present as $C_1$ to $C_6$ alkylene, $C_1$ to $C_6$ substituted alkylene, $C_7$ to $C_{12}$ phenylalkylene and $C_7$ to $C_{12}$ substituted phenylalkylene, provided that, when D is $—NR_{10}R_{11}—$ or $—C(O)NR_{10}R_{11}—$, $R_{11}$ is present and directly connected to the triazole ring;

In an additional preferred embodiment:

$R_4$ is the formula:

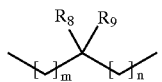

wherein:

$R_8$ and $R_9$ are together or independently a hydrogen atom, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ acyl, $C_1$ $C_7$ substituted acyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino or amino-protecting group; and m and n are independently 0, 1, 2, 3 or 4;

In a further preferred embodiment:

$R_5$ is absent or is a hydrogen atom, a halide, —OH, $—CO_2H$, —CHO, $—C(O)NR_{15}R_{16}$ and $—NR_{15}R_{16}$, wherein $R_{15}$ and $R_{16}$ are independently a hydrogen atom, $C_1$ to $C_6$ alkyl, $C_1$ to $C_6$ substituted alkyl, phenyl, substituted phenyl, heterocycle, substituted heterocycle, heteroaryl, substituted heteroaryl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, $C_7$ to $C_{12}$ phenylalkyl or $C_7$ to $C_{12}$ substituted phenylalkyl; or $R_5$ is $—NR_{15}R_{16}$, wherein $R_{15}$ and $R_{16}$ are $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl or substituted phenylaminothiocarbonyl.

In another preferred embodiment of the subject triazole compounds and combinatorial libraries:

$R_1$ combined with $R_2$ is 4-hydroxyphenyl, 3-chloro-4-hydroxyphenyl, 3-methoxy-4-hydroxyphenyl or 3-hydroxyphenyl;

$R_3$ is 4-methylphenyl, phenyl, 4-chlorophenyl, 3-nitrophenyl or 4-pyridino;

$R_4$ is ethylene, hexamethylene, 2-methylpropylene, -4-$(CH_2CH_2O)$ $C_6H_4CH_2—$ or -4-$(CH_2CH_2N(CH_2CH_3))$ $C_6H_4$ $CH_2—$; and $R_5$ is $—NR_{15}R_{16}$, wherein $R_{15}$ is a hydrogen atom; and $R_{16}$ is cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-aminooctyl, 2-trifluoromethylbenzyl, cyclopropyl, 2-thiophenemethyl, 1-indanyl, 4-(aminosulphonyl) phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, m-1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl) methyl, 3-methoxyphenethyl, 1,4-piperazino-bispropyl, L-1-(ethoxycarbonyl)ethyl, 4-aminocyclohexyl, 3,3-dimethylbutyl or methoxycarbonylmethyl.

In another preferred embodiment:

$R_1$ to $R_4$ are the above-described species substituents; and $R_5$ is $—NR_{15}R_{16}$, wherein $R_{15}$ is cyclobutanecarbonyl, 2-pyrazinecarbonyl, benzyloxyacetyl, 1-acetylpiperidine-4-carbonyl, 3,4-dimethoxybenzoyl, 2-fluoro-5-nitrobenzoyl, 2-chloro-5-(methylthio)benzoyl, 6-methylchromone-2-carbonyl, 2-methylcyclopropanecarbonyl, pyridine-3-carbonyl, (R)(-)α-methoxyphenylacetyl, 4-(dimethylamino)butyryl, 3-methoxybenzoyl, 4-chloro-3-nitrobenzoyl, 4-(methylthio)benzoyl, benzofuran-2-carbonyl, 2,2,3,3-tetramethylcyclopropanecarbonyl, 6-methylpyridine-3-carbonyl, 4-(methoxycarbonyl) benzoyl, L-2-pyrrolidone-5-carbonyl, piperonyloyl, 4-methoxy-3-nitrobenzoyl, 2-(methylthio)pyridine-3-carbonyl, 7-methoxy-2-benzofurancarbonyl, 4-methylpentanoyl, 6-hydroxy-pyridine-2-carbonyl, benzoyl, acetamidoacetyl, 4-phenoxybenzoyl, 4-nitrobenzoyl, 3,4-dichlorobenzoyl, 2-furancarbonyl, cyclopropanecarbonyl, 6-chloropyridine-2-carbonyl, 4-methylbenzoyl, 3-methylbutyryl, 3-phenoxybenzoyl, 3-methyl-4-nitrobenzoyl, 2-methoxy-4-(methylthio)-benzoyl, 3-methylbenzoyl, 3,5,5-trimethylhexanoyl, 5-bromo-pyridine-3-carbonyl, hydrocinnamoyl, cyclohexanepropionyl, 4-chloro-2-methoxybenzoyl, 2-fluorobenzoyl, 4-propylbenzoyl, 4-cyanobenzoyl, cyclopentylacetyl, 4-methoxy-2-quinolinecarbonyl, 4-isopropylbenzoyl, 4-pentenoyl, (3,4-dimethoxyphenyl)acetyl, 2,6-difluorobenzoyl, (phenylthio)acetyl, 3-cyanobenzoyl, octanoyl, 2-(allylthio)pyridine-3-carbonyl, p-tolylacetyl, 2-norbornaneacetyl, 4-ethoxyphenylacetyl, 3-nitrophenylacetyl, 4-pentylbenzoyl, 4-azidobenzoyl, 3-pyridinepropionyl, 1-naphthylacetyl, 4-carbonyl-1-(furfuryl)pyrrolidin-2-one, benzoylformyl, 4-fluorophenylacetyl, 4-cyclohexylbenzoyl, 3-benzoylpropionyl, acetyl, 3,4-dichlorophenylacetyl, α-methylcinnamoyl, cyclohexylidenecyanoacetyl, phenoxyacetyl, 2-chloro-4-fluorophenylacetyl, trans-2-phenyl-1-cyclopropanecarbonyl, 4-biphenylacetyl, trans-3-hexenoyl, 3-(trifluoromethyl)phenylacetyl, 4-bromophenylacetyl, tetrahydro-2-furoyl, 4-phenoxybutyryl, phthalimidoacetyl, 4-isopropylcinnamoyl, 3-methylindene-2-carbonyl, methoxyacetyl, 2-thiopheneacetyl, ethoxyacetyl, 2-ethyl-2-hexenoyl, 2-(2-(2-methoxyethoxy)ethoxy) acetyl, 3,4-dihydro-2,2-dimethyl-4-oxo-2H-pyran-6-carbonyl, (methylthio)acetyl or diethylphosphonoacetyl; and $R_{16}$ is cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl) phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl) methyl, 3-methoxyphenethyl, L-1-(ethoxycarbonyl) ethyl, 4-aminocyclohexyl, 3,3-dimethylbutyl or methoxycarbonylmethyl.

In a further preferred embodiment:
$R_1$ to $R_4$ are the above-described species substituents; and
$R_5$ is —$NR_{15}R_{16}$, wherein
$R_{15}$ is 2-mesitylenesulfonyl, 2-naphthalenesulfonyl, 2-thiophenesulfonyl, 4-methoxybenzenesulfonyl, benzenesulfonyl, 4-acetamidobenzenesulfonyl, p-toluenesulfonyl, 3,4-dimethoxybenzenesulfonyl, 3-chloro-4-fluorobenzenesulfonyl, 3-(trifluoromethyl)benzenesulfonyl, 4-ethylbenzenesulfonyl, 2-chloro-6-methylbenzenesulfonyl, 3,5-dichlorobenzenesulfonyl, 3-chlorobenzenesulfonyl, 3-fluorobenzenesulfonyl, 5-chloro-1,3-dimethylpyrazole-4-sulphonyl, 3,5-dimethylisoxazole-4-sulfonyl, 2-methoxycarbonylthiophene-3-sulphonyl, 5-chloro-2-methoxybenzenesulfonyl, 4-cyanobenzenesulfonyl, 3-cyanobenzesulphonyl, 3-chloro-4-methylbenzenesulphonyl, 2,4-difluorobenzenesulfonyl, 2-fluorobenzenesulfonyl, 4-isopropylbenzenesulfonyl, 2,5-dimethoxybenzenesulfonyl, 3,4-dichlorobenzenesulfonyl, 2,3,5,6-tetramethylbenzenesulfonyl, 2-chlorobenzenesulfonyl, 3-nitrobenzenesulfonyl, 4-acetylbenzenesulfonyl, 4-methyl-3-nitrobenzenesulfonyl, 4-n-butylbenzenesulfonyl, 4-nitrobenzenesulfonyl, 4-propylbenzenesulfonyl, 5-fluoro-2-methylbenzenesulfonyl, β-styrenesulfonyl, 4-chloro-2,5-dimethylbenzenesulphonyl, m-toluenesulfonyl or p-xylene-2-sulfonyl; and $R_{16}$ is cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl) phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl) methyl, 3-methoxyphenethyl, L-1-(ethoxycarbonyl) ethyl, 4-aminocyclohexyl, 3,3-dimethylbutyl or methoxycarbonylmethyl.

In an additional preferred embodiment:
$R_1$ to $R_4$ are the above-described species substituents; and
$R_5$ is —$NR_{15}R_{16}$, wherein
$R_{15}$ is trans-2-phenylcyclopropylaminocarbonyl, phenylaminocarbonyl, 2-bromophenylaminocarbonyl, 2-fluorophenylaminocarbonyl, 2,4-difluorophenylaminocarbonyl, 2,6-difluorophenylaminocarbonyl, 2-chlorophenylaminocarbonyl, 2,3-dichlorophenylaminocarbonyl, 2,4-dichlorophenylaminocarbonyl, 2,5-dichlorophenylaminocarbonyl, 2,6-dichlorophenylaminocarbonyl, 2-methoxyphenylaminocarbonyl, 2,4-dimethoxyphenylaminocarbonyl, 2,-dimethoxyphenylaminocarbonyl, 2-ethoxyphenylaminocarbonyl, 2-(trifluoromethyl) phenylaminocarbonyl, o-tolylaminocarbonyl, 2,6-dimethylphenylaminocarbonyl, 2-ethylphenylaminocarbonyl, 3-bromophenylaminocarbonyl, 3-fluorophenylaminocarbonyl, 3-chlorophenylaminocarbonyl, 3,4-dichlorophenylaminocarbonyl, 3-methoxyphenylaminocarbonyl, 3-(trifluoromethyl)phenylaminocarbonyl, m-tolylaminocarbonyl, 4-bromophenylaminocarbonyl, 4-fluorophenylaminocarbonyl, 4-chlorophenylaminocarbonyl, 4-methoxyphenylaminocarbonyl, 4-(ethoxycarbonyl)phenylaminocarbonyl, 4-(trifluoromethyl)phenylaminocarbonyl, p-tolylaminocarbonyl, benzoylaminocarbonyl, trichloroacetylaminocarbonyl, chloroacetylaminocarbonyl, t-butylaminocarbonyl, (s)-(−)-alpha-methylbenzylaminocarbonyl, isopropylaminocarbonyl, methylaminocarbonyl, octadecylaminocarbonyl, ethylaminocarbonyl, 2-chloroethylaminocarbonyl, allylaminocarbonyl, n-propylaminocarbonyl, n-butylaminocarbonyl, cyclohexylaminocarbonyl, 1-naphthylaminocarbonyl, (r)-(−)-1-(1-naphthyl)ethylaminocarbonyl, 4-fluoro-3-nitrophenylaminocarbonyl, 2-nitrophenylaminocarbonyl, 3-nitrophenylaminocarbonyl, 4-nitrophenylaminocarbonyl, 2,6-diisopropylphenylaminocarbonyl, benzylaminocarbonyl, trichloromethylaminocarbonyl, 3-chloropropylaminocarbonyl, ethoxycarbonylaminocarbonyl, 3,5-bis(trifluoromethyl)phenylaminocarbonyl, 2,5-difluorophenylaminocarbonyl, 2,4,5-trichlorophenylaminocarbonyl, 2,4,6-trichlorophenylaminocarbonyl, 2-(methoxycarbonyl)phenylaminocarbonyl, 2-(ethoxycarbonyl)phenylaminocarbonyl, 2-isopropylphenylaminocarbonyl, 2,3-dimethylphenylaminocarbonyl, 4-methoxy-2-methylphenylaminocarbonyl, 2,4-dimethylphenylaminocarbonyl, 2,5-dimethylphenylaminocarbonyl, 2-ethyl-6-methylphenylaminocarbonyl, 3-cyanophenylaminocarbonyl, 5-chloro-2,4-dimethoxyphenylaminocarbonyl, 3-chloro-4-methylphenylaminocarbonyl, 3,5-dichlorophenylaminocarbonyl, 2-methoxy-5-chlorophenylaminocarbonyl, 3,4,5-trimethoxyphenylaminocarbonyl, 3,5-dimethoxyphenylaminocarbonyl, 3-(methylthio)phenylaminocarbonyl, 3-(ethoxycarbonyl)phenylaminocarbonyl, 3-acetylphenylaminocarbonyl, 3,4-dimethylphenylaminocarbonyl, 3,5-dimethylphenylaminocarbonyl, 2-methoxy-5-methylphenylaminocarbonyl, 3-ethylphenylaminocarbonyl, 4-bromo-2-(trifluoromethyl)-phenylaminocarbonyl, 4-chloro-2-methoxyphenylaminocarbonyl, 4-chloro-2-(trifluoromethyl)-phenylaminocarbonyl, 4-chloro-3-(trifluoromethyl)-phenylaminocarbonyl, 4-iodophenylaminocarbonyl, 4-phenoxyphenylaminocarbonyl, 4-ethoxyphenylaminocarbonyl, 4-(methylthio)phenylaminocarbonyl, 4-acetylphenylaminocarbonyl, 4-isopropylphenylaminocarbonyl, 4-ethylphenylaminocarbonyl, 4-n-butylphenylaminocarbonyl, octylaminocarbonyl, 2-naphthylaminocarbonyl, 4-methyl-3-nitrophenylaminocarbonyl, 4-chloro-2-nitrophenylaminocarbonyl, 4-methyl-2-nitrophenylaminocarbonyl, 2-fluoro-5-nitrophenylaminocarbonyl, 2-methyl-5-nitrophenylaminocarbonyl, 3-bromopropylaminocarbonyl, 3-iodopropylaminocarbonyl, 5-bromopentylaminocarbonyl, 5-iodopentylaminocarbonyl, mesitylaminocarbonyl, 2-isopropyl-6-methylphenylaminocarbonyl, 2,6-diethylphenylaminocarbonyl, 5-chloro-o-tolylaminocarbonyl, 4-chloro-2-methylphenylaminocarbonyl, 4-(trifluoromethoxy)phenylaminocarbonyl, isobutylaminocarbonyl, 4-(trifluoromethylthio)-phenylaminocarbonyl, 2-chloro-5-(trifluoromethyl)-phenylaminocarbonyl, 2-chloro-6-methylphenylaminocarbonyl, 2,4,5-trimethylphenylaminocarbonyl, 2-methyl-6-t-butylphenylaminocarbonyl, 3-chloro-2-methoxyphenylaminocarbonyl, 3-chloro-2-methylphenylaminocarbonyl, 3-chloro-4-fluorophenylaminocarbonyl, 4-cyanophenylaminocarbonyl, 4-bromo-2-methylphenylaminocarbonyl, 4-bromo-2,6-dimethylphenylaminocarbonyl, 2,6-dibromo-4-fluorophenylaminocarbonyl, 4-n-butoxyphenylaminocarbonyl, 4-n-butoxycarbonylphenylaminocarbonyl, phenethylaminocarbonyl, 2-methyl-3-nitrophenylaminocarbonyl, hexylaminocarbonyl, hexadecylaminocarbonyl, 4-chloro-3-nitrophenylaminocarbonyl, 2-chloro-4-nitrophenylaminocarbonyl, 4,5-dimethyl-2-nitrophenylaminocarbonyl, 2-chloro-5-nitrophenylaminocarbonyl, 3-fluoro-4-methylphenylaminocarbonyl, 5-fluoro-2-methylphenylaminocarbonyl, 2-(methylthio)phenylaminocarbonyl, 3-carbomethoxyphenylaminocarbonyl, 2-biphenylylaminocarbonyl, 4-biphenylylaminocarbonyl, 4-(t-butyl)phenylaminocarbonyl, 1-(4-bromophenyl)ethylaminocarbonyl, n-butoxycarbonylmethylaminocarbonyl, dodecylaminocarbonyl, 2,6-dichloropyrid-4-ylaminocarbonyl, 2-(thien-2-yl)ethylaminocarbonyl, 2-bromo-4,6-difluorophenylaminocarbonyl, (r)-(+)-α-methylbenzylaminocarbonyl, 1-(1-naphthyl)ethylaminocarbonyl, (s)-(+)-1-(1-naphthyl)ethylaminocarbonyl, 3,4-difluorophenylaminocarbonyl, 2-methoxy-5-nitrophenylaminocarbonyl, 2-(chloromethyl)phenylaminocarbonyl, 3-isopropenyl-α,α-dimethylbenzylaminocarbonyl, 2-(trifluoromethoxy)phenylaminocarbonyl, 4-(chloromethyl)phenylaminocarbonyl, 1-adamantylaminocarbonyl, pentylaminocarbonyl, heptylaminocarbonyl, 2-bromoethylaminocarbonyl, 1,1,3,3-tetramethylbutylaminocarbonyl, 3,5-dinitrophenylaminocarbonyl, 4-(6-methyl-2-benzothiazolyl)-phenylaminocarbonyl, 2-iodophenylaminocarbonyl, 2-n-propylphenylaminocarbonyl, 4-benzyloxyphenylaminocarbonyl, 2-phenoxyphenylaminocarbonyl, 4-bromo-2-chlorophenylaminocarbonyl, 4-bromo-2-fluorophenylaminocarbonyl, 2-fluoro-5-methylphenylaminocarbonyl, 4-fluoro-2-nitrophenylaminocarbonyl, 2,3,4-trifluorophenylaminocarbonyl, 4-heptyloxyphenylaminocarbonyl, 4-dimethylaminophenylaminocarbonyl, 2-(difluoromethoxy)phenylaminocarbonyl, 4-(difluoromethoxy)phenylaminocarbonyl, 3-(trifluoromethylthio)phenylaminocarbonyl, 2-methylbenzylaminocarbonyl, 3-methylbenzylaminocarbonyl, 4-methylbenzylaminocarbonyl, 2-chlorobenzylaminocarbonyl, 4-fluorobenzylaminocarbonyl, 3,4-dichlorobenzylaminocarbonyl, 4-methoxybenzylaminocarbonyl, 2,6-difluorobenzoylaminocarbonyl, 4-fluorobenzoylaminocarbonyl, 2-fluoro-3-(trifluoromethyl)-phenylaminocarbonyl, 2-fluoro-5-(trifluoromethyl)-phenylaminocarbonyl, 2-fluoro-6-(trifluoromethyl)-phenylaminocarbonyl, 4-fluoro-2-(trifluoromethyl)-phenylaminocarbonyl, 4-fluoro-3-(trifluoromethyl)-phenylaminocarbonyl, 2-cyanophenylaminocarbonyl, 3-cyclopentoxy-4-methoxy-phenylaminocarbonyl, 2-t-butylphenylaminocarbonyl, 4-n-butyl-2-methylphenylaminocarbonyl, 2,6-dibromo-4-isopropylphenylaminocarbonyl or 3-pyridylaminocarbonyl; and $R_{16}$ is cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, L-1-(ethoxycarbonyl)ethyl, 4-aminocyclohexyl, 3,3-dimethylbutyl or methoxycarbonylmethyl.

In an additional preferred embodiment:

$R_1$ to $R_4$ are the above-described species substituents; and
$R_5$ is —$NR_{15}R_{16}$, wherein $R_{15}$ is methyl, ethyl, benzyl, butyl, trans cinnamyl, cyclohexyl, cyclopropyl, 2,2-diphenylethyl, hydrocinnamyl, isobutyl, isopentyl, 1,3,5-trimethylbenzyl, n-octyl, phenethyl, propyl, 2,2,2-trimethylethyl, n-pentyl, 1,2,3,6-tetrahydrobenzyl, 1,4-benzodioxan-6-methyl, 1-methyl-2-pyrrolemethyl, 1-methylindole-3-methyl, 1-naphthyl, 10-chloro-9-anthryl, 2,3,4-trifluorobenzyl, 2,3,5-trichlorobenzyl, 2,3-(methylenedioxy)benzyl, 2,3-difluorobenzyl, 2,4,5-trimethoxybenzyl, 2,4-dichlorobenzyl, 3,5-difluorobenzyl, 2,5-dimethylbenzyl, 2,6-difluorobenzyl, 2,6-dimethoxybenzyl, 2-bromobenzyl, 2-chloro-6-fluorobenzyl, 2-cyanobenzyl, 2-ethylbutyryl, 2-fluorobenzyl, 2-furyl, 2-methoxy-1-naphthyl, 2-methoxybenzyl, o-anisyl, 2-naphthyl, 2-pyridinemethyl, 2-quinolinemethyl, 2-thiophenemethyl, 3,3-dimethylbutyl, 3,4-(methylenedioxy)benzyl, 3,5,5-trimethylhexyl, 3,5-bis(trifluoromethyl)benzyl, 3,5-dibenzyloxybenzyl, 3,5-dichlorobenzyl, 3,5-dimethoxybenzyl, 3-(trifluoromethyl)benzyl, 3-fluoro-4-methoxybenzyl, 3-fluoro-p-anisyl, 3-fluorobenzyl, 3-furyl, 3-methoxybenzyl, m-anisyl, 3-methyl-4-methoxybenzyl, 2-methylbenzyl, 3-methylbenzyl, m-toluyl, 3-phenylbutyl, 3-pyridinemethyl, 3-quinolinemethyl, 3-thiophenemethyl, 4-(methylthio)benzyl, 4-(trifluoromethyl)benzyl, 4-acetamidobenzyl, 4-methoxybenzyl, 4-benzyloxybenzyl, 4-biphenylmethyl, 4-cyanobenzyl, 4-fluorobenzyl, 4-isopropylbenzyl, 4-methoxy-1-naphthyl, 2,4-dimethoxy-3-methylbenzyl, 4-methylbenzyl, p-toluyl, 4-propoxybenzyl, 4-pyridinemethyl, 4-quinolinemethyl, 5-methyl-2-thiophenemethyl, 5-methyl-2-furyl, 6-methyl-2-pyridinemethyl, pyrrole-2-methyl, 2,4-dimethoxybenzyl, 2,3,4-trimethoxybenzyl, 2,2-dimethyl-4-pentenyl, 3-methoxy-2-nitrobenzyl, 2,5-dimethoxybenzyl, 2-(4-chlorophenylthio)benzyl, 2-methylbutyl, 2-methylpentyl, 2-chlorobenzyl, 2-(trifluoromethyl)benzyl, 2-benzyloxy-3-methoxy-benzyl, 2-phenylpropyl, 3,4,5-trimethoxybenzyl, 3-(methylthio)propyl, 3-chloro-4-fluorobenzyl, 3-chlorobenzyl, 3-methoxy-4,5-methylenedioxybenzyl, 3-methyl-2-butenyl, 4-(diethylamino)benzyl, 4-(trifluoromethoxy)benzyl, 4-acetoxybenzyl, 4-chlorobenzyl, 4-pyrrolidinobenzyl, 5-methylbenzo-b-thiophene-2-methyl, indole-3-methyl, 2-fluoro-3-(trifluoromethyl)benzyl, 2-thiazolemethyl, 4,5-dimethyl-2-furyl, 4-t-butylbenzyl, phenanthrene-9-methyl, 5-(4-chlorophenyl)furfuryl, 3-bromo-4-methoxybenzyl, 5-ethyl-2-furyl, 5-chloro-2-thiophenemethyl, 4-ethylbenzyl, 2,4-diethoxy-m-toluyl, 3-methyl-2-thiophenemethyl, 4-ethoxybenzyl, 2,6-dimethyl-5-heptenyl, 2-chloro-3,4-dimethoxybenzyl, 3,4-diethoxybenzyl, 4-chloro-3-fluorobenzyl, 3-methyl-p-anisyl or 3-methylbutyl; and $R_{16}$ is cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, L-1-(ethoxycarbonyl)ethyl, 4-aminocyclohexyl, 3,3-dimethylbutyl or methoxycarbonylmethyl.

The invention also provides methods for making triazole compounds and libraries. In one method of the invention, triazole compounds can be prepared by (a) coupling a hydroxy ester to a solid support, such as a resin via the hydroxy moiety (see FIG. 1); (b) transforming the ester moiety to an acyl hydrazine by reacting the ester with a hydrazino compound (see FIG. 2); and (c) forming the triazole ring compound by reacting the acyl hydrazine with an amidino compound (see FIG. 3).

Another method further includes reacting the resin bound triazole compound with an electrophile. Such an electrophile can include an alcohol, aldehyde or an alkyl substituted with one or more halides (see FIG. 4).

Figure 4:
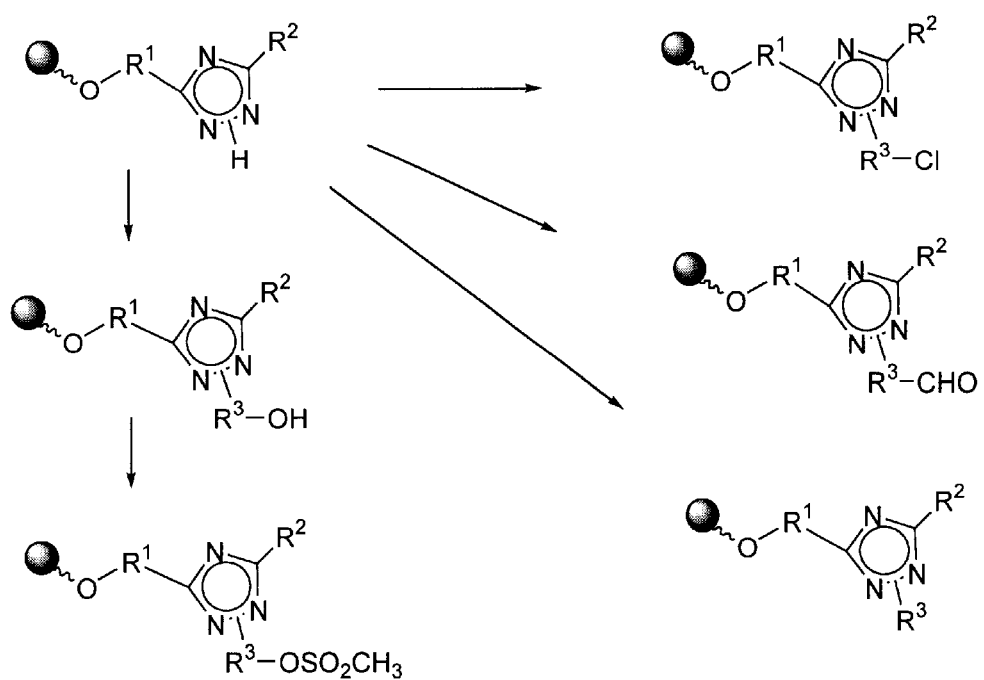

When the electrophile contains an alcohol moiety, the resulting triazole alcohol compound can be further reacted with a sulfonyl compound to form a triazole sulfonyl compound (see FIG. 4).

Figure 5:
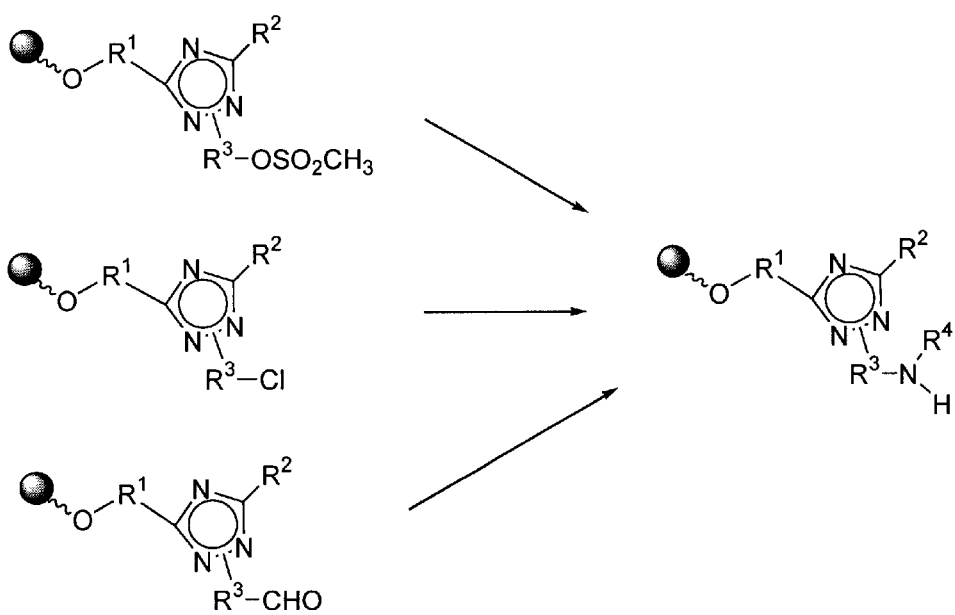
Figure 6:
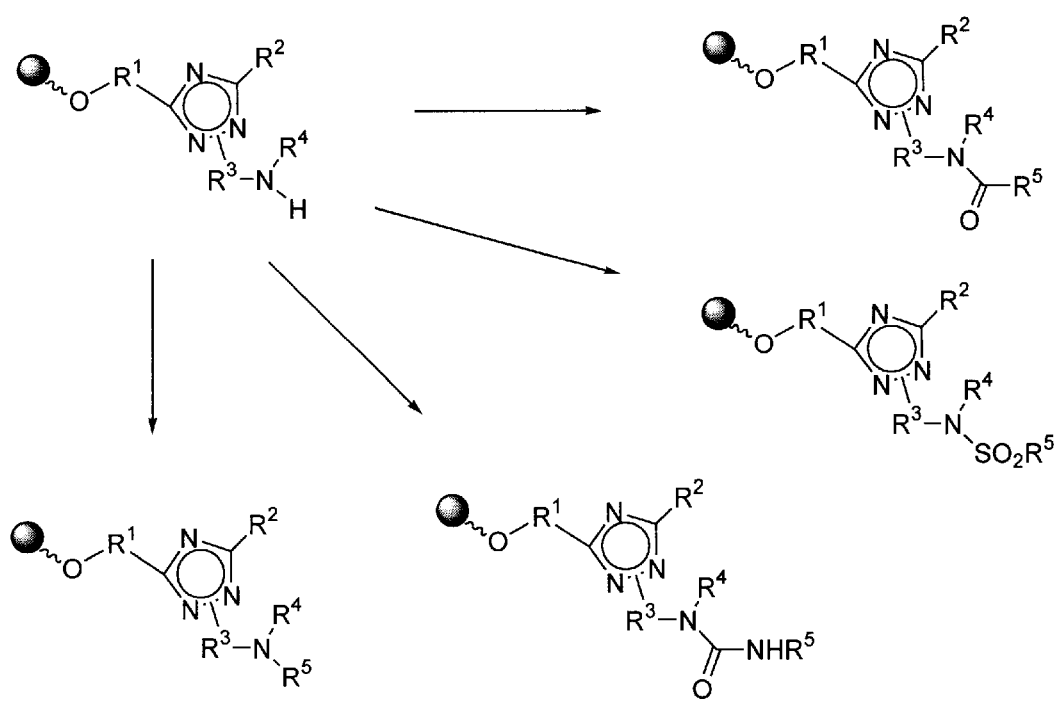

An additional method of making triazole compounds and libraries further includes aminating the triazole compound (see FIG. 5). Other methods further include (a) acylating the amino portion of the amino triazole compound; (b) sulfonating the amino portion of the amino triazole compound; (c) reacting the amino portion of the amino triazole compound with an isocyanate compound; or (d) reductively alkylating the amino portion of the amino triazole compound (see FIG. 6).

When the above-described compounds include one or more chiral centers, the stereochemistry of such chiral centers can independently be in the R or S configuration, or a mixture of the two. The chiral centers can be further designated as R or S or R,S or d,D, l,L or d,l, D,L.

Regarding the compounds and combinatorial libraries described herein, the suffix "ene" added to any of the described terms means that the substituent is connected to two other parts in the compound.

The term "$C_1$ to $C_6$ alkyl" denotes such radicals as methyl, ethyl, n-propyl, isopropyl, n-butyl, iso-butyl, sec-butyl, tert-butyl, amyl, tert-amyl, hexyl and the like. The preferred "$C_1$ to $C_6$ alkyl" groups are methyl, ethyl, iso-butyl, sec-butyl and iso-propyl. Similarly, the term "$C_1$ to $C_{12}$ alkylene" denotes radicals of 1 to 12 carbons.

The term "$C_2$ to $C_7$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_7$ alkynyl" denotes such radicals as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl as well as di- and tri-ynes of straight and branched chains.

The terms "$C_1$ to $C_6$ substituted alkyl," "$C_2$ to $C_7$ substituted alkenyl," "$C_2$ to $C_7$ substituted alkynyl," and "$C_1$ to $C_{12}$ substituted alkylene" denote that the above $C_1$ to $C_6$ alkyl groups and $C_2$ to $C_7$ alkenyl and $C_2$ to $C_7$ alkynyl groups and $C_1$ to $C_{12}$ alkylene are substituted by one or more, and preferably one or two, halogen, hydroxy, protected hydroxy, oxo, protected oxo, $C_3$ to $C_7$ cycloalkyl, naphthyl, amino, protected amino, (monosubstituted)amino, protected (monosubstituted)amino, (disubstituted)amino, guanidino, protected guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "$C_2$ to $C_7$ alkenylene" as used herein denotes an alkene group that is linked by two different substitutents. Similarly, the term "$C_2$ to $C_7$ alkynylene" as used herein denotes an alkyne group that is linked by two different substitutents. The term "$C_2$ to $C_7$ substituted alkenylene" as used herein denotes an alkene group that is linked by two different substitutents and is further substituted by one or two halogen, hydroxy, protected hydroxy, oxo, protected oxo, $C_3$ to $C_7$ cycloalkyl, naphthyl, amino, protected amino, (monosubstituted)amino, protected (monosubstituted)amino, (disubstituted)amino, guanidino, protected guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_7$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_7$ substituted alkoxy" means the alkyl portion of the alkoxy can be substituted in the same manner as in relation to $C_1$ to $C_6$ substituted alkyl. Similarly, the term "$C_1$ to $C_7$ phenylalkoxy" as used herein means "$C_1$ to $C_7$ alkoxy" bonded to a phenyl radical.

The term "$C_1$ to $C_7$ acyloxy" denotes herein groups such as formyloxy, acetoxy, propionyloxy, butyryloxy, pivaloyloxy, pentanoyloxy, hexanoyloxy, heptanoyloxy and the like.

Similarly, the term "$C_1$ to $C_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "$C_1$ to $C_7$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_6$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_7$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "$C_3$ to $C_7$ cycloalkyl" includes the cyclopropyl, cyclobutyl, cyclopentyl, cyclohexyl or cycloheptyl rings. Similarly, the term "$C_5$ to $C_7$ cycloalkyl" includes the cyclopentyl, cyclohexyl or cycloheptyl rings.

The substituent term "$C_3$ to $C_7$ substituted cycloalkyl" or "$C_5$ to $C_7$ substituted cycloalkyl" indicates the above cycloalkyl rings substituted by one or two halogen, hydroxy, protected hydroxy, $C_1$ to $C_4$ alkylthio, $C_1$ to $C_4$ alkylulfoxide $C_1$ to $C_1$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy, oxo, protected oxo, (monosubstituted)amino, (disubstituted)amino, trifluoromethyl, carboxy, protected carboxy, phenyl, substituted phenyl, phenylthio, phenylsulfoxide phenylsulfonyl, amino, or protected amino groups.

The term "$C_3$ to $C_7$ cycloalkylene" means a cycloalkyl, as defined above, where the cycloalkyl radical is bonded at two positions connecting together two separate additional groups. Similarly, the term "$C_3$ to $C_7$ substituted cycloalkylene" means a cycloalkylene where the cycloalkyl radical is bonded at two positions connecting together two separate additional groups and further bearing at least one addltional substituent.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical, halogen, hydroxy, protected hydroxy, $C_1$ to $C_7$ alkoxy, trifluoromethyl, carboxy, protected carboxy, oxo, protected oxo, (monosubstituted)amino, protected (monosubstituted) amino, (disubstituted)amino, phenyl, substituted phenyl, amino, or protected amino.

The term "$C_5$ to $C_7$ cycloalkenylene" is a cycloalkenyl ring, as defined above, where the cycloalkenyl radical is bonded at two positions connecting together two separate additional groups. Similarly, the term "substituted $C_5$ to $C_7$ cycloalkenylene" means a cycloalkenylene further substituted by halogen, hydroxy, protected hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The term "heterocycle" or "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully saturated or partially unsaturated, with fully saturated rings being preferred. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophen-yl.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N—($C_1$ to $C_6$ alkyl) carboxamide, protected N—($C_1$ to $C_1$ alkyl)carboxamide, N, N-di($C_1$ to $C_6$ alkyl)carboxamide, trifluoromethyl, N—(($C_1$ to $C_6$ alkyl)sulfonyl)amino or N-(phenylsulfonyl)amino groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, phthalimido, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N, N-di($C_1$ to $C_6$ alkyl)carboxamide, trifluoromethyl, N—(($C_1$ to $C_1$ alkyl)sulfonyl)amino or N-(phenylsulfonyl)amino groups.

The term "$C_7$ to $C_{12}$ phenylalkyl" denotes a $C_1$ to $C_6$ alkyl group substituted at any position by a phenyl, substituted phenyl, heteroaryl or substituted heteroaryl. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, (monosubstituted) amino, protected (monosubstituted)amino, (disubstituted) amino, guanidino, protected guanidino, heterocyclic ring, substituted heterocyclic ring, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, nitro, carboxy, protected carboxy, carbamoyl, carboxamide, protected carboxamide, N—($C_1$ to $C_6$ alkyl) carboxamide, protected N—($C_1$ to $C_6$ alkyl) carboxamide, N,N—($C_1$ to $C_6$ dialkyl) carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N, N-di($C_1$ to $C_6$ alkyl)carboxamide, trifluoromethyl, N—(($C_1$ to $C_6$ alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "$C_7$ to $C_{12}$ phenylalkylene" specifies a $C_7$ to $C_{12}$ phenylalkyl, as defined above, where the phenylalkyl radical is bonded at two positions connecting together two separate additional groups. The definition includes groups of the formula: -phenyl-alkyl- and -alkyl-phenyl-alkyl-. Substitutions on the phenyl ring can be 1,2, 1,3 or 1,4. The term "$C_7$ to $C_{12}$ substituted phenylalkylene" means a $C_7$ to $C_{12}$ phenylalkylene as defined above that is further substituted by halogen, hydroxy, protected hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy, oxo, protected oxo, (monosubstituted)amino, (disubstituted) amino, trifluoromethyl, carboxy, protected carboxy, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl) carboxamide, N, N-di($C_1$ to $C_6$ alkyl)carboxamide, trifluoromethyl, N—(($C_1$ to $C_6$ alkyl)sulfonyl)amino, N-(phenylsulfonyl)amino or phenyl, wherein the phenyl is substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2,3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenoxy" denotes a phenyl bonded to an oxygen atom. The term "substituted phenoxy" specifies a phenoxy group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, carboxamide, protected carboxamide, N—($C_1$ to $C_6$ alkyl)carboxamide, protected N—($C_1$ to $C_6$ alkyl)carboxamide, N, N-di($C_1$ to $C_6$ alkyl) carboxamide, trifluoromethyl, N—(($C_1$ to $C_6$ alkyl)sulfonyl) amino and N-(phenylsulfonyl)amino.

Examples of substituted phenoxy include 2-methylphenoxy, 2-ethylphenoxy, 2-propylphenoxy, 2-isopropylphenoxy, 2-sec-butylphenoxy, 2-tert-butylphenoxy, 2-allylphenoxy, 2-propenylphenoxy, 2-cyclopentylphenoxy, 2-fluorophenoxy, 2-(trifluoromethyl) phenoxy, 2-chlorophenoxy, 2-bromophenoxy, 2-methoxyphenoxy, 2-ethoxyphenoxy, 2-isopropoxyphenoxy, 3-methylphenoxy, 3-ethylphenoxy, 3-isopropylphenoxy, 3-tert-butylphenoxy, 3-pentadecylphenoxy, 3-(trifluoromethyl)phenoxy, 3-fluorophenoxy, 3-chlorophenoxy, 3-bromophenoxy, 3-iodophenoxy, 3-methoxyphenoxy, 3-(trifluoromethoxy) phenoxy, 4-methylphenoxy, 4-ethylphenoxy, 4-propylphenoxy, 4-isopropylphenoxy, 4-sec-butylphenoxy, 4-tert-butylphenoxy, 4-tert-amylphenoxy, 4-nonylphenoxy, 4-dodecylphenoxy, 4-cyclopenylphenoxy, 4-(trifluoromethyl)phenoxy, 4-fluorophenoxy, 4-chlorophenoxy, 4-bromophenoxy, 4-iodophenoxy, 4-methoxyphenoxy, 4-(trifluoromethoxy)phenoxy, 4-ethoxyphenoxy, 4-propoxyphenoxy, 4-butoxyphenoxy, 4-hexyloxyphenoxy, 4-heptyloxyphenoxy, 2,3-dimethylphenoxy, 5,6,7,8-tetrahydro-1-naphthoxy, 2,3-dichlorophenoxy, 2,3-dihydro-2,2-dimethyl-7-benzofuranoxy, 2,3-dimethoxyphenoxy, 2,6-dimethylphenoxy, 2, 6-diisopropylphenoxy, 2,6-di-sec-butylphenoxy, 2-tert-butyl-6-methylphenoxy, 2,6-di-tert-butylphenoxy, 2-allyl-6-methylphenoxy, 2,6-difluorophenoxy, 2,3-difluorophenoxy, 2,6-dichlorophenoxy, 2,6-dibromophenoxy, 2-fluoro-6-methoxyphenoxy, 2,6-dimethoxyphenoxy, 3,5-dimethylphenoxy, 5-isopropyl-3-methylphenoxy, 3,5-ditert-butylphenoxy, 3,5-bis(trifluoromethyl)phenoxy, 3,5-difluorophenoxy, 3,5-dichlorophenoxy, 3,5-dimethoxyphenoxy, 3-chloro-5-methoxyphenoxy, 3,4-dimethylphenoxy, 5-indanoxy, 5,6,7,8-tetrahydro-2-naphthoxy, 4-chloro-3-methylphenoxy, 2,4-dimethylphenoxy, 2,5-dimethylphenoxy, 2-isopropyl-5-methylphenoxy, 4-isopropyl-3-methylphenoxy, 5-isopropyl-2-methylphenoxy, 2-tert-butyl-5-methylphenoxy, 2-tert-butyl-4-methylphenoxy, 2,4-di-tert-butylphenoxy, 2,4-di-tert-amylphenoxy, 4-fluoro-2-methylphenoxy, 4-fluoro-3-methylphenoxy, 2-chloro-4-methylphenoxy, 2-chloro-5-methylphenoxy, 4-chloro-2-methylphenoxy, 4-chloro-3-ethylphenoxy, 2-bromo-4-methylphenoxy, 4-iodo-2-methylphenoxy, 2-chloro-5-(trifluoromethyl)phenoxy, 2,4-difluorophenoxy, 2,5-difluorophenoxy, 3,4-difluorophenoxy, 4-chloro-2-fluorophenoxy, 3-chloro-4-fluorophenoxy, 4-chloro-3-fluorophenoxy, 2-bromo-4-fluorophenoxy, 4-bromo-2-fluorophenoxy, 2-bromo-5-fluorophenoxy, 2,4-dichlorophenoxy, 3,4-dichlorophenoxy, 2,5-dichlorophenoxy, 2-bromo-4-chlorophenoxy, 2-chloro-4-fluorophenoxy, 4-bromo-2-chlorophenoxy, 2,4-dibromophenoxy, 2-methoxy-4-methylphenoxy, 4-allyl-2-methylphenoxy, trans-2-ethoxy-5-(1-propenyl)phenoxy, 2-methoxy-4-propenylphenoxy, 3,4-dimethoxyphenoxy, 3-ethoxy-4-methoxyphenoxy, 4-allyl-2,6-dimethoxyphenoxy, 3,4-methylenedioxyphenoxy, 2,3,6-trimethylphenoxy, 2,4-dichloro-3-methylphenoxy, 2,3,4-trifluorophenoxy, 2,3,6-trifluorophenoxy, 2,3,5-trifluorophenoxy, 2,3,4-trichlorophenoxy, 2,3,6-trichlorophenoxy, 2,3,5-trimethylphenoxy, 3,4,5-trimethylphenoxy, 4-chloro-3,5-dimethylphenoxy, 4-bromo-3,5-dimethylphenoxy, 2,4,6-trimethylphenoxy, 2,6-bis(hydroxymethyl)-4-methylphenoxy, 2,6-di-tert-butyl-4-methylphenoxy, 2,6-di-tert-butyl-4-methoxyphenoxy, 2,4,5-trifluorophenoxy, 2-chloro-3,5-difluorophenoxy, 2,4,6-trichlorophenoxy, 3,4,5-trimethoxyphenoxy, 2,3,5-trichlorophenoxy, 4-bromo-2,6-dimethylphenoxy, 4-bromo-6-chloro-2-methylphenoxy, 2,6-dibromo-4-methylphenoxy, 2,6-dichloro-4-fluorophenoxy, 2,6-dibromo-4-fluorophehoxy, 2,4,6-tribromophenoxy, 2,4,6-triiodophenoxy, 2-chloro-4,5-dimethylphenoxy, 4-chloro-2-isopropyl-5-methylphenoxy, 2-bromo-4,5-difluorophenoxy, 2,4,5-trichlorophenoxy, 2,3,5,6-tetrafluorophenoxy and the like.

The term "$C_7$ to $C_{12}$ substituted phenylalkoxy" denotes a $C_7$ to $C_{12}$ phenylalkoxy group wherein the $C_1$ to $C_6$ alkyl portion is substituted with one or more, and preferably one or two, groups selected from halogen, hydroxy, protected hydromy, oxo, protected oxo, amino, protected amino, (monosubstituted)amino, protected (monosubstituted) amino, (disubstituted)amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—($C_1$ to $C_6$ alkyl) carboxamide, N, N—($C_1$ to $C_6$ dialkyl)carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group can be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, carboxamide, protected carboxamide, N—($C_1$ to $C_6$ alkyl) carboxamide, protected N—($C_1$ to $C_6$ alkyl) carboxamide, N, N-di($C_1$ to $C_1$ alkyl) carboxamide, trifluoromethyl, N—(($C_1$ to $C_6$ alkyl) sulfonyl) amino, N-(phenylsulfonyl)amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkoxy" include groups such as 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, (+/−)-2-phenyl-1-propoxy, 2,2-dimethyl-3-phenyl-1-propoxy and the like.

The term "phthalimide" means a cyclic imide which is made from phthalic acid, also called 1,2-benzenedicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N, N-di($C_1$ to $C_6$ alkyl)carboxamide, trifluoromethyl, N—(($C_1$ to $C_6$ alkyl)sulfonyl)amino and N-(phenylsulfonyl)amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl) carboxamide, N, N-di($C_1$ to $C_6$ alkyl)carboxamide, trifluoromethyl, N—(($C_1$ to $C_6$ alkyl)sulfonyl)amino or N-(phenylsulfonyl) amino.

Examples of the term "substituted naphthyl" includes a mono or di(halo)naphthyl group such as 1, 2, 3, 4, 5, 6, 7 or 8-chloronaphthyl, 2, 6-dichloronaphthyl, 2, 5-dichloronaphthyl, 3, 4-dichloronaphthyl, 1, 2, 3, 4, 5, 6, 7 or 8-bromonaphthyl, 3, 4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2, 4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1, 2, 4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)naphthyl group, for example, 2, 6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2, 4-di(-protected carboxy)naphthyl; a mono-or di(hydroxymethyl)naphthyl or (protected hydroxymethyl) naphthyl such as 1, 2, 3, 4, 5, 6, 7 or 8-(protected hydroxymethyl)naphthyl or 3, 4-di(hydroxymethyl) naphthyl; a mono- or di(amino)naphthyl or (protected amino)naphthyl such as 1, 2, 3, 4, 5, 6, 7 or 8-(amino) naphthyl or 2, 4-(protected amino)-naphthyl, a mono- or di(aminomethyl)naphthyl or (protected aminomethyl) naphthyl such as 2, 3, or 4-(aminomethyl)naphthyl or 2, 4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The term "naphthylene" means a naphthyl radical bonded at two positions connecting together two separate additional groups. Similarly, the term "substituted napthylene" means a naphthylene group that is further substituted by halogen, hydroxy, protected hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The terms "halo" and "halogen" refer to the fluoro, chloro, bromo or iodo atoms. There can be one or more halogen, which are the same or different. Preferred halogens are chloro and fluoro.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_1$ to $C_7$ substituted acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino."

The term "(disubstituted)amino" refers to an amino group with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_6$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on no the carboxamide nitrogen. Similarly, the term "protected N—($C_1$ to $C_6$ alkyl) carboxamide" means there is an amino-protecting group on the carboxamide nitrogen.

Examples of such amino-protecting groups include the formyl ("For") group, the trityl group, the phthalimido group, the trichloroaqetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethokycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, -2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "protected guanidino" as used herein refers to an "amino-protecting group" on one or two of the guanidino nitrogen atoms. Examples of "protected guanidino" groups are described by T. W. Greene and P. G. M. Wuts; M. Bodanzsky; and Stewart and Young, supra.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, -(trimethylsilyl)ethyl, -(di(n-butyl)methylsilyl)ethyl, p-toluenesublonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4'-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydroxymethyl" which refer to a hydroxy or hydroxymethyl substituted with one of the above hydroxy-protecting groups.

The term "$C_1$ to $C_4$ alkylthio" refers to sulfide groups such as methylthio, ethylthio, n-propylthio, isopropylthio, n-butylthio, t-butylthio and like groups.

The term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_4$ alkylsulfonyl" encompasses groups such as methylsulfonyl, ethylsulfonyl, n-propylsulfonyl, isopropylsulfonyl, n-butylsulfonyl, t-butylsulfonyl and the like.

The terms "$C_1$ to $C_4$ substituted alkylthio," "$C_1$ to $C_4$ substituted alkylsulfoxide," and "$C_1$ to $C_4$ substituted alkylsulfonyl," denote the $C_1$ to $C_4$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_6$ alkylaminocarbonyl" means a $C_1$ to $C_6$ alkyl attached to a nitrogen of the aminocarbonyl group. Examples of $C_1$ to $C_6$ alkylaminocarbonyl include methylaminocarbonyl (from methylisocyanate), ethylaminocarbonyl (from ethylisocyanate), propylaminocarbonyl (from propylisocyanate), butylaminocarbonyl (from butylisocyatate). The term "$C_1$ to $C_6$ substituted alkylaminocarbonyl" denotes a substituted alkyl bonded to a nitrogen of the aminocarbonyl group, which alkyl may be substituted as described above in relation to $C_1$ to $C_6$ substituted alkyl. Examples of $C_1$ to $C_6$ substituted alkylaminocarbonyl include, for example, methoxymethylaminocarbonyl (from methoxymethylisocyanate), 2-chloroethylaminocarbonyl (from 2-chloroethylisocyanate), 2-oxopropylaminocarbonyl (from 2-oxopropylisocyanate), and 4-phenylbutylaminocarbonyl (from phenylbutylisocyanate).

The term "$C_1$ to $C_7$ alkoxycarbonyl" means a "$C_1$ to $C_7$ alkoxy" group attached to a carobonyl group. The term "$C_1$ to $C_7$ substituted alkoxycarbonyl" denotes a substituted alkoxy bonded to the carbonyl group, which alkoxy may be substituted as described above in relation to $C_1$ to $C_6$ substituted alkyl.

The term "phenylaminocarbonyl" means a phenyl attached to a nitrogen of the aminocarbonyl group. The term "substituted phenylaminocarbonyl" denotes a substituted phenyl bonded to a nitrogen of the aminocarbonyl group, which phenyl may be substituted as described above in relation to substituted phenyl. Examples of substituted phenylaminocarbonyl include 2-chlorophenylaminocarbonyl (from 2-chlorophenylisocyanate), 3-chlorophenylaminocarbonyl (from 3-chlorophenylisocyanate), 2-nitorphenylaminocarbonyl (from 2-nitrophenylisocyanate), 4-biphenylaminocarbonyl (from 4-biphenylisocyanate), and 4-methoxyphenylaminocarbonyl (from 4-methoxyphenylisocyanate).

The term "$C_1$ to $C_6$ alkylaminothiocarbonyl" means a $C_1$ to $C_6$ alkyl attached to an aminothiocarbonyl group, wherein the alkyl has the same meaning as defined above. Examples of $C_1$ to $C_6$ alkylaminothiocarbonyl include methylaminothiocarbonyl (from methylisothiocyanate), ethylaminothiocarbonyl (from ethylisothiocyanate), propylaminothiocarbonyl (from propylilsothiocyanate), butylaminothiocarbonyl (from butylisothiocyatate).

The term "$C_1$ to $C_6$ substituted alkylaminothiocarbonyl" denotes a substituted alkyl bonded to an aminothiocarbonyl group, wherein the alkyl may be substituted as described above in relation to $C_1$ to $C_6$ substituted alkyl. Examples of $C_1$ to $C_6$ substituted alkylaminothiocarbonyl include, for example, methoxymethylaminothiocarbonyl (from methoxymethylisothiocyanate), 2-chloroethylaminothiocarbonyl (from 2-chloroethylisothiocyanate), 2-oxopropylaminothiocarbonyl (from 2-oxopropylisothiocyanate), and 4-phenylbutylaminothiocarbonyl (from phenylbutylisothiocyanate).

The term "phenylaminothiocarbonyl" means a phenyl attached to an aminothiocarbonyl group, wherein the phenyl has the same meaning as defined above.

The term "substituted phenylaminothiocarbonyl" denotes a substituted phenyl bonded to an aminothiocarbonyl group, wherein phenyl may be substituted as described above in relation to substituted phenyl. Examples of substituted phenylaminothiocarbonyls include 2-chlorophenylaminothiocarbonyl (from 2-chlorophenylisothiocyanate), 3-chlorophenylaminothiocarbonyl (from 3-chlorophenylisothiocyanate), 2nitorphenylaminothiocarbonyl (from 2-nitrophenylisothiocyanate), 4-biphenylaminothiocarbonyl (from 4-biphenylisothiocyanate), and 4-methoxyphenylaminothiocarbonyl (from 4-methoxyphenylisothiocyanate).

The term "phenylene" means a phenyl group where the phenyl radical is bonded at two positions connecting together two separate additional groups. Examples of "phenylene" includes 1,2-phenylene, 1,3-phenylene, and 1,4-phenylene.

The term "substituted $C_1$ to $C_{12}$ alkylene" means a $C_1$ to $C_{12}$ alkyl group where the alkyl radical is bonded at two positions connecting together two separate additional groups and further bearing an additional substituent. Examples of "substituted $C_1$ to $C_{12}$ alkylene" includes aminomethylene, 1-(amino)-1,2-ethyl, 2-(amino)-1,2-ethyl, 1-(acetamido)-1,2-ethyl, 2-(acetamido)-1,2-ethyl, 2-hydroxy-1,1-ethyl, 1-(amino)-1,3-propyl.

The term "substituted phenylene" means a phenyl group where the phenyl radical is bonded at two positions connecting together two separate additional groups, wherein the phenyl is substituted as described above in relation to "substituted phenyl."

The terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstituted)amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups which contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means an —NCO— group where the radical is bonded at two positions connecting two separate additional groups.

One or more of the compounds of the invention, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1–19 (1977), which is incorporated herein by reference. Other cations encompassed by the above term include the protonated form of procaine, quinine and N-methylglucosamine, and the protonated forms of basic amino acids such as glycine, ornithine, hisatidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more compounds of the invention, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the -($C_1$ to $C_7$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_4$ alkylthiomethyl groups, for example methylthiomethyl, ethylthiomethyl, isopropylthiomethyl and the like; the acyloxymethyl groups, for example pivaloyloxymethyl, pivaloyloxyethyl, -acetoxymethyl and the like; the ethoxycarbonyl-1-methyl group; the -acetoxyethyl; the 1-($C_1$ to $C_7$ alkyloxycarbonyloxy)ethyl groups such as the 1-(ethoxycarbonyloxy)ethyl group; and the 1-($C_1$ to $C_7$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The term "functionalized resin" means any resin, crosslinked or otherwise, where functional groups have been introduced into the resin, as is common in the art. Such resins include, for example, those functionalized with amino, alkylhalo, formyl or hydroxy groups. Such resins which can serve as solid supports are well known in the art and include, for example, 4-methylbenzhydrylamine-copoly (styrene-1% divinylbenzene) (MBHA), 4-hydroxymethylphenoxymethyl-copoly(styrene-1% divinylbenzene), 4-oxymethyl-phenyl-acetamido-copoly (stryene-1% divinylbenzene)(Wang), 4-(oxymethyl)-phenylacetamido methyl (Pam), and Tentagel™, from Rapp Polymere Gmbh, trialkoxy-diphenyl-methyl ester-copoly (styrene-1% divinylbenzene)(RINK) all of which are commercially available. Other functionalized resins are known in the art and can be use without departure from the scope of the current invention. Such resins may include those described in Jung, G., Combinatorial Peptide and Nonpeptide Libraries, A Handbook (VCH Verlag, 1996) or Bunin, B. A., The Combinatorial Index (Academic Press, 1998) and are incorporated herein by reference.

As used herein, a "combinatorial library" is an intentionally created collection of differing molecules which can be prepared by the means provided below or otherwise and screened for biological activity in a variety of formats (e.g., libraries of soluble molecules, libraries of compounds attached to resin beads, silica chips or other solid supports). A "combinatorial library," as defined above, involves successive rounds of chemical syntheses based on a common starting structure. The combinatorial libraries can be screened in any variety of assays, such as those detailed below as well as others useful for assessing their biological activity. The combinatorial libraries will generally have at least one active compound and are generally prepared such that the compounds are in equimolar quantities.

Compounds disclosed in previous work that are not disclosed as part of a collection of compounds or not disclosed as intended for use as part of such a collection are not part of a "combinatorial library" of the invention. In addition, compounds that are in an unintentional or undesired mixture are not part of a "combinatorial library" of the invention.

A combinatorial library of the invention can contain two or more of the above-described compounds. The invention further provides a combinatorial library containing three, four or five or more of the above-described compounds. In another embodiment of the invention, a combinatorial library can contain ten or more of the above-described compounds. In yet another embodiment of the invention, a combinatorial library can contain fifty or more of the above-described compounds. If desired, a combinatorial library of the invention can contain 100,000 or more, or even 1,000,000 or more, of the above-described compounds.

By way of example, the preparation of the combinatorial libraries can use the "split resin approach." The split resin approach is described by, for example, U.S. Pat. No. 5,010,175 to Rutter, WO PCT 91/19735 to Simon, and Gallop et al., J. Med. Chem., 37:1233–1251 (1994), all of which are incorporated herein by reference.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration or the D-amino acid can readily be substituted for that in the L-configuration.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active triazole. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

As pharmaceutical compositions for treating infections, pain, or any other indication the compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

The compounds of and combinatorial libraries containing the same can be prepared as set forth in FIGS. 1 to 6 and described below.

Variant triazole combinatorial libraries can be prepared in order to achieve a high level of diversity. For instance, a variety of hydroxyl esters can be attached to solid support by a range of methods (see FIG. 1 and Example 1). More specifically, phenols with an ester moiety were loaded to Wang resin via Mitsunobu reaction, or to Bromo Wang resin by substitution reaction. Aliphatic alcohols with an ester moiety were similarly loaded to Bromo Wang or Wang trichloroacetimidate resin (see Hanessian and Xie, *Tetrahedron Letters*, 39:733–736 (1998), which is incorporated herein by reference).

Other esters can be loaded to a solid support in various alternate ways. For example, a cleavable amino resin can be reacted with haloalkylesters, or by coupling the carboxylic acid group of diacid monoesters to a resin-bound amine via an amide bond (e.g., methylbenzhydrylamine (MBHA)).

Figure 2:
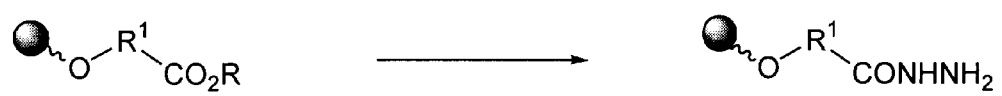
Figure 3:
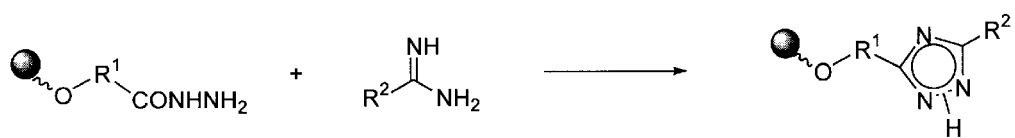

The resulting resin-bound ester can then be transformed to an acyl hydrazine (see FIG. 2 and Example 2). The acyl hydrazine can then be cyclized into a triazole by a range of methods(see FIG. 3 and Example 3).

The triazole can then be reacted with an electrophile. Such an electrophile can include one containing a range of moieties such as any one of a variety of alcohols, aldehydes or alkyls substituted with one or more halides. When the electrophile is an alcohol, the resulting triazole-alcohol can be transformed into the corresponding mesylate. See FIG. 4 and Example 4.

The mesylate, halide or triazole-aldehyde made by the previous reaction can then be aminated using one of a variety of amines. See FIG. 5 and Example 5. The reulting amino-triazolo can then be further derivatized, for example, by acylation (using one of a variety of carboxylic acids; see Example 8), sulfonation (using one of a variety of sulfonyl halides; see Example 9), by reacting with one of a variety of isocyanates (see Example 10) or by reductive alkylation (see Example 11). See also FIG. 6 and Example 6.

Resin-bound triazoles can be cleaved from the resins by treating them with trifluoroacetic acid (TFA)/DCM solution. After extraction and lyophilization, non-support bound triazole compounds can be obtained. See Example 12.

Triazole compounds and libraries, such as those of the present invention, can be made utilizing individual polyethylene bags, referred to as "tea bags" (see Houghten et al., *Proc. Natl. Acad. Sci. USA* 82: 5131 (1985); *Biochemistry*, 32:11035 (1993); and U.S. Pat. No. 4,631,211, all of which are incorporated herein by reference).

The nonsupport-bound combinatorial libraries can be screened as single compounds. In addition, the nonsupport-bound combinatorial libraries can be screened as mixtures in solution in assays such as radio-receptor inhibition assays, anti-bacterial assays, anti-fungal assays, calmodulin-dekpendent phosphodiosterase (CaMPDE) assays and phosphodiesterase (PDE) assays, as described in detail below. Deconvolution of highly active mixtures can then be carried out by iterative or positional scanning methods. These techniques, the iterative approach or the positional scanning approach, can be utilized for finding other active compounds within the combinatorial libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various combinatorial libraries as described, for example, in R. Houghten et al. PCT/US91/08694 and U.S. Pat. No. 5,556,762, both of which are incorporated herein by reference. In the positional scanning approach, sublibraries are made defining only one variable with each set of sublibraries and all possible sublibraries with each single variable defined (and all other possibilities at all of the other variable positions), made and tested. From the instant description one skilled in the art could synthesize combinatorial libraries wherein two fixed positions are defined at a time. From the testing of each single-variable defined combinatorial library, the optimum substituent at that position can be determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the compounds, as well as methods of using the same, are included within the scope of the present invention. The compounds of the present invention can be used for a variety of purposes and indications and as medicaments for any such purposes and indications. For example, as described above, triazole compounds of the present invention can be used as pesticides, acaricides, receptor agonists or antagonists and antimicrobial agents, including antibacterial or antiviral agents. Additionally, the subject compounds can be useful as analgesics. Assays which can be used to test the biological activity of the instant compounds include antimicrobial assays, a competitive enzyme-linked immunoabsorbent assay and radio-receptor assays, as described below.

The ability of the compounds to inhibit bacterial growth, and therefore be useful to that infection, can be determined by methods well known in the art. Compounds of the present invention were shown to have antimicrobial activity by the in vitro antimicrobial activity assay described below and, therefore, are useful as antimicrobial agents.

In addition, an exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 μl of the culture solution using serial dilutions (e.g., $10^{-2}$, $10^{-3}$ and $10^{-4}$) onto solid agar lates. In 96-well tissue culture plates, compounds, individual or in mixtures, are added to the bacterial suspension at concentrations derived from serial two-fold dilutions ranging from 1500 to 2.9 μl. The plates are incubated overnight at 37° C. and the growth determined at each concentration by $OD_{620}$ nm. The $IC_{50}$ (the concentration necessary to inhibit 50% of the growth of the bacteria) can then be calculated.

The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 μl. After blocking, 25 μl of a 1.0 mg/ml solution of each mixture of a synthetic combinatorial library (or individual compound) is added, followed by MAb 125-10F3 (Appel et al., supra) (25 μl per well). The MAb is added at a fixed dilution in which the bicyclic guanidine in solution effectively competes for MAb binding with the antigenic peptide adsorbed to the plate. The remaining steps are the same as for direct ELISA. The concentration of compound necessary to inhibit 50% of the MAb binding to the control peptide on the plate ($IC_{50}$) is determined by serial dilutions of the compound.

Alternative screening can be done with radio-receptor assays. The radio-receptor assay, can be selective for any one of the μ, κ, or δ opiate receptors. Compounds of the present invention can be useful in vitro for the diagnosis of relevant opioid receptor subtypes, such as κ, in the brain and other tissue samples. Similarly, the compounds can be used in vivo diagnostically to localize opioid receptor subtypes.

The radio-receptor assays are also an indication of the compounds' analgesic properties as described, for example, in Dooley et al., *Proc. Natl. Acad. Sci.,* 90:10811–10815 (1993). For example, it can be envisioned that these compounds can be used for therapeutic purposes to block the peripheral effects Of a centrally acting pain killer. For instance, morphine is a centrally acting pain killer. Morphine, however, has a number of deleterious effects in the periphery which are not required for the desired analgesic effects, such as constipation and pruritus (itching). While it is known that the many compounds do not readily cross the blood-brain barrier and, therefore, elicit no central effect, the subject compounds can have value in blocking the periphery effects of morphine, such as constipation and pruritus. Accordingly, the subject compounds can also be useful as drugs, namely as analgesics, or to treat pathologies associated with other compounds which interact with the opioid receptor system.

Additionally, such compounds can be tested in a σ receptor assay. Ligands for the σ receptor can be useful as antipsychotic agents, as described in Abou-Gharbia et al., *Annual Reports in Medicinal Chemistry,* 28:1–10 (1993).

Radio-receptor assays can be performed with particulate membranes prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC5C SA-600: Du Pont, Wilmington, Del.) (16,000 rpm) for 10 minutes. The pellets are resuspended in fresh Tris-HCl buffer and incubated at 37° C. for 40 minutes. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in Bradford, M. M., *Anal. Biochem.* 72:248–254 (1976), which is incorporated herein by reference.

Binding assays are carried out in polypropylene tubes, each tube containing 0,5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 μg/ml of bicyclic guanidine, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the bicyclic guanidines, individually or in mixtures.

IC$_{50}$ values (the concentration necessary to inhibit 50% of $^3$H-DAMGO binding) are then calculated. IC$_{50}$ values of less than 1000 nM are indicative of highly active opioid compounds which bind to the p receptor, with particularly active compounds having IC$_{50}$ values of 100 nM or less and the most active compounds with values of less than 10 nM.

As opposed to this p receptor selective assay, which can be carried out using $^3$H-DAMGO as radioligand, as described above, assays selective for κ receptors can be carried out using [$^3$H]-U69,593 (3 nM, specific activity 62 Ci/mmol) as radioligand. Assays selective for δ opiate receptors can be carried out using tritiated DSLET ([D-Ser$^2$, D-Leu$^5$]-threonine-enkephalin) as radioligand. Assays selective for the σ opiate receptor can use radiolabeled pentazocine as ligand.

Screening of combinatorial libraries and compounds of the invention can be done with an anti-fungal assay. Compounds of the present invention can be useful for treating fungal infections.

Screening of combinatorial libraries and compounds of the invention also can be done with a calmodulin-dependent phosphodiesterase (CaMPDE) assay. Compounds of the present invention can be useful as calmodulin antagonists.

Calmodulin (CaM), which is the major intracellular calcium receptor, is involved in many processes that are crucial to cellular viability. In particular, calmodulin is implicated in calcium-stimulated cell proliferation. Calmodulin antagonists are, therefore, useful for treating conditions associated with increased cell proliferation, for example, cancer. In addition, calmodulin antagonists such as compounds of the subject invention are useful both in vitro and in vivo for identifying the role of calmodulin in other biological processes. The disadvantages of known antagonists such as trifluoperazine and N—(4-aminobutyl)-5-chloro-2-naphthalenesulfonamide (W13) include their non-specificity and toxicity. In contrast, advantages of the combinatorial libraries and compounds of the subject invention as calmodulin antagonists include their reduced flexibility and ability to generate broader conformational space of interactive residues as compared to their linear counterparts.

An example of an assay that identifies CaM antagonists is a CaMPDE assay. In brief, samples are mixed with 50 μl of assay buffer (360 mM Tris, 360 mM Imidazole, 45 mM Mg(CH$_3$COO)$_{21}$ pH 7.5) and 10 μl of CaCl$_2$ (4.5 mM) to a final volume of 251 μl. 25 μl of calmodulin stock solution (Boehringer Mannheim; 0.01 μg/μl) is then added and the samples then sit at room temperature for 10 minutes. 14 μl of PDE (Sigma; 2 Units dissolved in 4 ml of water; stock concentration: 0.0005 Units/μl) is then added, followed by 50 μl of 5'-nucleotidase (Sigma; 100 Units dissolved in 10 ml of 10 mM Tris-HCl containing 0.5 mM Mg(CH$_3$COO)$_2$, pH 7.0; stock concentration: 10 Units/ml). The samples are then incubated for 10 minutes at 30° C. 50 μl of adenosine 3',5'-cyclic monophosphate (cAMP) (20 mM in water at pH 7.0) is added, the samples incubated for 1 hour at 30° C. and then vortexed. 200 μl of trichloroacetic acid (TCA) (55% in water) is added to a 200 μl sample aliquot, which is then vortexed and centrifuged for 10 minutes. 80 μl of the resulting supernatants of each sample is transferred to a 96-well μlate, with 2 wells each containing 80 μl of each sample. 80 μl of ammonium molybdate (1.1% in 1.1N H$_2$SO$_4$) is then added to all the wells, and the OD of each were determined at 730 nm, with the values later subtracted to the final OD reading. 16 μl of reducing agent (6 g sodium bisulfite, 0.6 g sodium sulfite and 125 mg of 1-amino-2-naphtol-4-sulfonic acid in 50 ml of water) is then added to one of each sample duplicate and 16 μl of water is added to the other duplicate. After sitting for 1 hour at room temperature, the OD of each well is determined at 730 nm. The percent inhibition of calmodulin activity is then calculated for each sample, using as 0% inhibition a control sample containing all reagents without any test samples and as 100% inhibition a control sample containing test samples and all reagents except calmodulin. In addition, the percent inhibition of phosphodiesterase activity was determined by following a similar protocol as the CaMPDE assay described above, except not adding calmodulin to the sample mixture and calculating the percent inhibition by using as 0% inhibition a control reagent without any test samples and as 100% inhibition a control sample containing test samples and all reagents except cAMP.

The following examples are provided to illustrate but not limit the present invention.

EXAMPLE 1

Loading Hydroxy Esters to Solid Support

Example (a)

Wang resin (100 g) was suspended in N-methylmorpholine (NMM, 1400 mL), and an appropriate hydroxybenzoate (0.45 mol) and triphenylphosphine (Ph$_3$P, 0.45 mol) were added. After the mixture was cooled to 0° C., a solution diisopropylazodicarboxylate (DIAD, 0.45 mol) in NMM was added. Then the mixture was shaken for 40 h, the resin was washed with DMF (3×), CH$_2$Cl$_2$ (3×), and MeOH (3×), and dried under vacuum.

Example (b)

Resin-bound p-alkoxybenzyl trichloracetimidate was first prepared as described by Hanessian and Xie, *Tetrahedron Letters*, 39:733–736 (1998), which is incorporated herein by reference. This resin was then reacted with a hydroxyalkyl ester in the presence of BF$_3$ Et$_2$O in cyclohexane/DCM (1:1). The resin was washed with DMF (3×), CH$_2$Cl$_2$ (3×), and MeOH (3×), and dried under vacuum.

Example (c)

4-hydroxybenzoate was treated with t-BuOK in DMA for 30 min to form the phenol anion, which was mixed with a suspension of Bromo-Wang resin in DMA. The mixture was shaken at 50° C. overnight. The resin was then washed by DMF (3×), CH$_2$Cl$_2$ (3×), and MeOH (3×), and dried under vacuum.

EXAMPLE 2

Transformation of Resin-Bound Esters to Acyl Hydrazines

An ester resin (300 g; prepared as described above in Example 1) was mixed with NH$_2$NH$_2$.H$_2$O (99%, 600 mL) in 2-methoxyethanol (600 mL) and N-methylpyrrolidinone (NMP) (600 mL) and was shaken at 75° C. for 2 days. The resulting solution was cooled to RT. The resin was then washed by MeOH (2×), CH$_2$Cl$_2$ (3×), and MeOH (3×), and dried under vacuum.

EXAMPLE 3

Triazole Ring Formation on Solid Support

Example (a)

An acyl hydrazine resin prepared as described in Example 2 and was added to a solution of neutralized aryl/heteroaryl amidine in 2-methoxyethanol, followed by 1,8-diazabicyclo (5.4.0.)undec-7-ene (DBU). The mixture was heated at 75° C. for 1–2 days and washed by DMF (3×), $CH_2Cl_2$ (3×), and MeOH (3×), and dried under vacuum.

Example (b)

An acyl hydrazine resin prepared as described in Example 2 and was added to a solution of neutralized aryl amidine in 2-methoxyethanol, followed by $K_2CO_3$. The mixture was heated at 100° C. for 1–3 days and washed by DMF (1×), $DMF/H_2O$ (1:1, 2×), DMF (2×), $CH_2Cl_2$ (3×), and MeOH (3×), and dried under vacuum.

Example (c)

An acyl hydrazine resin prepared as described in Example 2 and was added to a solution of neutralized alkyl amidine in 2-methoxyethanol, followed by $K_2CO_3$ or 4 Å molecular sieves. The mixture was shaken at RT for 1 day and then heated at 100° C. for 2–24 h. After being cooled, the resin was washed by DMF (1×), $DMF/H_2O$ (1:1, 2×), DMF (2×), $CH_2Cl_2$ (3×), and MeOH (3×), and dried under vacuum.

EXAMPLE 4

Reactions of Resin-Bound Triazoles with Electrophiles

Example (a)

A triazole resin made as described in Example 3 (100 mg, 0.06 mmol) was suspended in NMP (10 mL). 2-bromoethanol and tetramethylguanidine (TMG) (10 mmol each) were then added and the mixture was shaken for 24 h. The resin was washed by DMF (3×), $CH_2Cl_2$ (3×), and MeOH (3×), and dried under vacuum.

Example (b)

A triazole resin made as described in Example 3 was suspended in NMP. 1-bromo-3-chloro-2-methylpropane and TMG were then added and the mixture was shaken for 40 h. The resin was washed by DMF (3×), $CH_2Cl_2$ (3×), and MeOH (3×), and dried under vacuum.

Example (c)

A triazole resin made as described in Example 3 was reacted with p-[(2-chloroethyl) ethylamino]benzaldehyde (0.5 M), TMG (0.5 M), and KI (0.25 M) in NMP at 50° C. for 40 h. The resin was washed by DMF (3×), $CH_2Cl_2$ (3×), and MebH (3×), and dried under vacuum.

Example (d)

A triazole resin made as described in Example 3 was reacted with p-(2-chloroethoxy) benzaldehyde (0.5 M) or 4-$(CH_3O_2SOCH_2CH_2O)C_6H_4CHO$, TMG (0.5 M), and KI (0.25 M) in NMP at 50° C. for 40 h. The resin was washed by DMF (3×), $CH_2Cl_2$ (3×), and MeOH (3×), and dried under vacuum.

Example (e)

A triazole resin made as described in Example 3 was suspended in DMF. Ground sodium hydroxide and an alkyl bromide were then added. The mixture was shaken at RT for 5–24 h. The resulting resin was washed by $DMF/H_2O$ (1:1, 2×), MeOH (2×), $CH_2Cl_2$ (1×), MeOH (1×), and $CH_2Cl_2$ (3×) and dried under vacuum to give a tri-substituted triazole resin.

Example (f)

The triazole-alcohols made as described in Example (a) (resin in tea bags) were transformed into the corresponding mesylates using $CH_3SO_2Cl$ and DIEA (all 0.25 M) in DCM at room temperature overnight (15–18 h).

EXAMPLE 5

Amination of Triazole Derivatives

Example (a)

The mesylates made as described in Example 4(f) were reacted with a primary amine (1 M) in NMP at 50 or 70° C. for 24–40 h to afford an amino-triazole resin, which was washed by DMF (3×), $CH_2Cl_2$ (3×), and MeOH (3×), and dried under vacuum.

Example (b)

General procedure for reductive amination of triazole-aldehydes. Triazole-aldehydes made as described in Examples 4(c) and 4(d) were reacted with primary amine (0.25 M) in mixed solvents $THF-AcOH-H_2O$ (90:5:5) at RT for 30–60 min, and then with $NaCNBH_3$ (0.25 M) at RT overnight. The resulting secondary amine resins were obtained after washing by DMF (3×), $CH_2Cl_2$ (3×), and MeOH (3×), and drying under vacuum.

Example (c)

The chloro-triazoles made as described in Example 4(b) were reacted with a primary amine (1 M) and KI (0.25 M) in NMP at 50 or 70° C. for 24–40 h to afford an amino-triazole resin, which was washed by DMF (3×) $CH_2Cl_2$ (3×) and MeOH (3×), and dried under vacuum.

EXAMPLE 6

Derivatization of Amino-Triazoles

Example (a)

Acylation—General Procedure: For amino-triazoles made as described in Example 5 (35 μmol), 700 μL of $RCO_2H$/DIEA/DCM-DMF (0.4 M, 0.28 mmol $RCO_2H$; 0.8M, 0.56 mmol DIEA; 2:1 DCM-DMF) and 350 μL of PyBOP/DCM-DMF (0.8 M, 0.28 mmol PyBOP; 2:1 DCM-DMF) were added and the mixture shaken at RT overnight (15–18 h). The resin was then washed by THF (2×), DMF (5×), MeOH (2×), THF (2×), and MeOH (4×) and dried.

Example (b)

Sulfonation—General Procedure:

For amino-triazoles made as described in Example 5 (35 μmol), 200 μL of 2.5M NMM/0.25M NMI/THF (0.55 mmol base) and 700 μL of $RSO_2Cl$/ACN (0.36 M, 0.25 mmol $RSO_2Cl$) were and added, and the mixture shaken at RT overnight (15–18 h). The resin was then washed by ACN (4×), THF (3×), and MeOH (4×) and dried.

Example (c)

Reaction with Isocyanates—General Procedure: Amino-triazoles made as described in Example 5 are suspended in DCE/THF (2:1) and treated with isocyanates (0.2 M) at RT overnight. The resin is washed with DCE/THF (2;1), DMF, and MeOH and dried to afford triazole-urea derivatives.

Example (d)

Reductive alkylation—General Procedure: Amino-triazoles made as described in Example 5 are suspended in THF—AcOH—H₂O or DMF-trimethylorthoformate and treated with various aldehydes followed by reduction using NaCNBH₃ or borane-amine complex. The resin is then washed by DMF, DMF/H₂O (2×), DMF, DCM (3×), MeOH (3×) and dried.

EXAMPLE 7

Preparation of a Combinatorial Library of Amino-triazole Compounds

Four hydroxyesters (methyl 4-hydroxybenzoate, methyl 3-chloro-4-hydroxybenzoate, methyl 3-methoxy-4-hydroxybenzoate and methyl 3-hydroxybenzoate) were coupled to Wang resin to form the ester resins, using the procedure described in Example 1. All of ester resins were converted into the acyl hydrazine resins as described in Example 2, and then each cyclized with five aryl amidines (4-methylbenzamidine hydrochloride, benzamidine hydrochloride, 4-chlorobenzamidine hydrochloride, 3-nitrobenzamidine hydrochloride and 4-amidinopyridine hydrochloride) to give twenty triazole resins, following procedure described in Example 3.

A set of 500 resin bound amino triazoles with a MW of less than 550 was selected from a possible 3000 combinations. According to this 500-set list, the resin bound triazoles were separated into 4 or 5 groups that react with one of five electrophiles (2-bromoethanol, 6-bromo-1-hexanol, 1-bromo-3-chloro-2-methylpropane, 4-(2-chloroethoxy) benzaldehyde and 4-((2-chloroethyl)ethylamino) benzaldehyde) to give further resin bound triazole compounds (following Example 4; see also FIG. 4), which were again split into different groups to react with 33 different amines to form 500 resin bound amino triazoles (as described in Example 5). The amines used were as follows:

Cyclopentylamine
Heptylamine
4-fluorobenzylamine
1-(3-aminopropyl)imidazole
3-chlorobenzylamine
3,3'-diamino-n-methyldipropylamine
1,8-diamino-3,6-dioxaoctane
2-trifluoromethylbenzylamine
Cyclopropylamine
2-thiophenemethylamine
1-aminoindan
4-(2-aminoethyl)benzenesulfonamide
3-ethoxypropylamine
3-(methylthio)propylamine
3-butoxypropylamine
N-(3'-aminopropyl)-2-pyrrolidinone
N-(2-aminoethyl)-n-ethyl-m-toluidine
B-methylphenethylamine
3,5-dimethoxybenzylamine
3-fluoro-5-(trifluoromethyl)benzylamine
Meso-1,2-diphenylethylenediamine
H-gly-obzl.p-tosylate
Dehydroabietylamine acetate
2-methylcyclohexylamine
4-bromophenethylamine
Isobutylamine
2-(aminomethyl)-1-ethyl-pyrrolidine
3-methoxyphenethylamine
1,4-bis(3-aminopropyl)piperazine
L-alanine ethyl ester hydrochloride
1,4-cyclohexanediamine
3,3-dimethylbutylamine
Glycine methyl ester hydrochloride

EXAMPLE 8

Preparation of a Combinatorial Library of Acylated Amino-triazole Compounds

Among the 500 resin bound amino triazoles described in Example 7, 420 were selected according to their predicted ability to react with carboxylic acids. Each of these 420 resin bound amino triazoles was distributed in equal amounts into each well of a 96 well plate, and then reacted with 96 carboxylic acids to afford the 4,320 member combinatorial library. The caroxylic acids used were as follows:

Cyclobutanecarboxylic acid
2-pyrazinecarboxylic acid
Benzyloxyacetic acid
1-acetylpiperidine-4-carboxylic acid
3,4-dimethoxybenzoic acid
2-fluoro-5-nitrobenzoic acid
2-chloro-5-(methylthio)benzoic acid
6-methylchromone-2-carboxylic acid
2-methylcyclopropanecarboxylic acid
Nicotinic acid
(R)-(−)-alpha-methoxyphenylacetic acid
4-(dimethylamino)butyric acid hydrochloride
M-anisic acid
4-chloro-3-nitrobenzoic acid
4-(methylthio)benzoic acid
Benzofuran-2-carboxylic acid
2,2,3,3-tetramethylcyclopropanecarboxylic acid
6-methylnicotinic acid
Mono-methyl terephthalate
L-2-pyrrolidone-5-carboxylic acid
Piperonylic acid
4-methoxy-3-nitrobenzoic acid
2-(methylthio)nicotinic acid
7-methoxy-2-benzofurancarboxylic acid
4-methylvaleric acid
6-hydroxypicolinic acid
Benzoic acid
N-acetylglycine
4-phenoxybenzoic acid
4-nitrobenzoic acid
3,4-dichlorobenzoic acid
2-furoic acid
Cyclopropanecarboxylic acid
6-chloronicotinic acid
P-toluic acid
Isovaleric acid
3-phenoxybenzoic acid
3-methyl-4-nitrobenzoic acid
2-methoxy-4-(methylthio)-benzoic acid
M-toluic acid 3,5,5-trimethylhexanoic acid
5-bromonicotinic acid
Hydrocinnamic acid
Cyclohexanepropionic acid
4-chloro-o-anisic acid
2-fluorobenzoic acid
4-n-propylbenzoic acid
4-cyanobenzoic acid
Cyclopentylacetic acid
4-methoxy-2-quinolinecarboxylic acid
4-isopropylbenzoic acid
4-pentenoic acid
(3,4-dimethoxyphenyl)acetic acid
2,6-difluorobenzoic acid
(Phenylthio)acetic acid
3-cyanobenzoic acid
Octanoic acid
2-(allylthio)nicotinic acid
P-tolylacetic acid
2-norbornaneacetic acid
4-ethoxyphenylacetic acid
3-nitrophenylacetic acid
4-pentylbenzoic acid
4-azidobenzoic acid
3-pyridinepropionic acid
1-naphthylacetic acid
4-carboxy-1-(furfuryl)pyrrolidin-2-one
Benzoylformic acid
4-fluorophenylacetic acid
4-cyclohexylbenzoic acid
3-benzoylpropionic acid
Acetic acid
3,4-dichlorophenylacetic acid
Alpha-methylcinnamic acid
Cyclohexylidenecyanoacetic acid
Phenoxyacetic acid
2-chloro-4-fluorophenylacetic acid
Trans-2-phenyl-1-cyclopropanecarboxylic acid
4-biphenylacetic acid
Trans-3-hexenoic acid
(Alpha-alpha-alpha-trifluoro-m-tolyl)acetic acid
4-bromophenylacetic acid
Tetrahydro-2-furoic acid
4-phenoxybutyric acid
N-phthaloylglycine
4-isopropylcinnamic acid
3-methylindene-2-carboxylic acid
Methoxyacetic acid
2-thiopheneacetic acid
Ethoxyacetic acid
2-ethyl-2-hexenoic acid
2-(2-(2-methoxyethoxy)ethoxy)acetic acid
4-dihydro-2,2-dimethyl-4-oxo-2H-pyran-6-carboxylic acid
Methylthioacetic acid
Diethylphosphonoacetic acid

EXAMPLE 9

Preparation of a Combinatorial Library of Sulfonated Amino-triazole Compounds 420 resin bound amino triazoles were prepared as described in Example 7. Each of the 420 resin bound amino triazoles was then reacted with 40 sulphonyl chlorides to form the 16,800 member combinatorial library. The sulfonyl chlorides used were as follows:
  2-mesitylenesulfonyl chloride
  2-naphthalenesulfonyl chloride
  2-thiophenesulfonyl chloride
  4-methoxybenzenesulfonyl chloride
  Benzenesulfonyl chloride
  4-acetamidobenzenesulfonyl chloride
  p-toluenesulfonyl chloride
  3,4-dimethoxybenzenesulfonyl chloride
  3-chloro-4-fluorobenzenesulfonyl chloride
  3-(trifluoromethyl)benzenesulfonyl chloride
  4-ethylbenzenesulfonyl chloride
  2-chloro-6-methylbenzenesulfonyl chloride
  3,5-dichlorobenzenesulfonyl chloride
  3-chlorobenzenesulfonyl chloride
  3-fluorobenzenesulfonyl chloride
  5-chloro-1,3-dimethylpyrazole-4-sulphonyl chloride
  3,5-dimethylisoxazole-4-sulfonyl chloride
  Methyl 3-chlorosulfonylthiophene-2-carboxylate
  5-chloro-2-methoxybenzenesulfonyl chloride
  4-cyanobenzenesulfonyl chloride
  3-cyanobenzenesulphonyl chloride
  3-chloro-4-methylbenzenesulphonyl chloride
  2,4-difluorobenzenesulfonyl chloride
  2-fluorobenzenesulfonyl chloride
  4-isopropylbenzenesulfonyl chloride
  2,5-dimethoxybenzenesulfonyl chloride
  3,4-dichlorobenzenesulfonyl chloride
  2,3,5,6-tetramethylbenzenesulfonyl chloride
  2-chlorobenzenesulfonyl chloride
  3-nitrobenzenesulfonyl chloride
  4-acetylbenzenesulfonyl chloride
  4-methyl-3-nitrobenzenesulfonyl chloride
  4-n-butylbenzenesulfonyl chloride
  4-nitrobenzenesulfonyl chloride
  4-n-propylbenzenesulfonyl chloride
  5-fluoro-2-methylbenzenesulfonyl chloride
  Beta-styrene sulfonyl chloride
  4-chloro-2,5-dimethylbenzenesulphonyl chloride
  m-toluenesulfonyl chloride
  p-xylene-2-sulfonyl chloride

EXAMPLE 10

Preparation of a combinatorial library of amino-triazole compounds reacted with isocyanates 420 resin bound amino triazoles are prepared as described in Example 7. Each of the 420 resin bound amino triazoles is then reacted with 200 different isocyanates to form the 84,000 member combinatorial library. The 200 isocyanates are as follows:
  trans-2-phenylcyclopropyl isocyanate
  phenyl isocyanate
  2-bromophenyl isocyanate
  2-fluorophenyl isocyanate
  2,4-difluorophenyl isocyanate
  2,6-difluorophenyl isocyanate 2-chlorophenyl isocyanate
2,3-dichlorophenyl isocyanate
2,4-dichlorophenyl isocyanate
2,5-dichlorophenyl isocyanate
2,6-dichlorophenyl isocyanate
2-methoxyphenyl isocyanate
2,4-dimethoxyphenyl isocyanate
2,5-dimethoxyphenyl isocyanate
2-ethoxyphenyl isocyanate
2-(trifluoromethyl)phenyl isocyanate
o-tolyl isocyanate
2,6-dimethylphenyl isocyanate
2-ethylphenyl isocyanate
3-bromophenyl isocyanate
3-fluorophenyl isocyanate
3-chlorophenyl isocyanate
3,4-dichlorophenyl isocyanate
3-methoxyphenyl isocyanate
3-(trifluoromethyl)phenyl isocyanate
m-tolyl isocyanate
4-bromophenyl isocyanate
4-fluorophenyl isocyanate
4-chlorophenyl isocyanate
4-methoxyphenyl isocyanate
ethyl 4-isocyanatobenzoate
4-(trifluoromethyl)phenyl isocyanate
p-tolyl isocyanate
benzoyl isocyanate
trichloroacetyl isocyanate
chloroacetyl isocyanate
tert-butyl isocyanate
(S)-(−)-alpha-methylbenzyl isocyanate
isopropyl isocyanate
methyl isocyanate
octadecyl isocyanate
ethyl isocyanate
2-chloroethyl isocyanate
allyl isocyanate
n-propyl isocyanate
n-butyl isocyanate
cyclohexyl isocyanate
1-naphthyl isocyanate
(R)-(−)-1-(1-naphthyl)ethyl isocyanate
4-fluoro-3-nitrophenyl isocyanate
2-nitrophenyl isocyanate
3-nitrophenyl isocyanate
4-nitrophenyl isocyanate
2,6-diisopropylphenyl isocyanate
benzyl isocyanate
trichloromethyl isocyanate
3-chloropropyl isocyanate
ethoxycarbonyl isocyanate
3,5-bis(trifluoromethyl)phenyl isocyanate
2,5-difluorophenyl isocyanate
2,4,5-trichlorophenyl isocyanate
2,4,6-trichlorophenyl isocyanate
methyl 2-isocyanatobenzoate
ethyl 2-isocyanatobenzoate
2-isopropylphenyl isocyanate
2,3-dimethylphenyl isocyanate
4-methoxy-2-methylphenyl isocyanate
2,4-dimethylphenyl isocyanate
2,5-dimethylphenyl isocyanate
2-ethyl-6-methylphenyl isocyanate
3-cyanophenyl isocyanate
5-chloro-2,4-dimethoxyphenyl isocyanate
3-chloro-4-methylphenyl isocyanate
3,5-dichlorophenyl isocyanate
2-methoxy-5-chloro phenyl isocyanate
3,4,5-trimethoxyphenyl isocyanate
3,5-dimethoxyphenyl isocyanate
3-(methylthio)phenyl isocyanate
ethyl 3-isocyanatobenzoate
3-acetylphenyl isocyanate
3,4-dimethylphenyl isocyanate
3,5-dimethylphenyl isocyanate
2-methoxy-5-methylphenyl isocyanate
3-ethylphenyl isocyanate
4-bromo-2-(trifluoromethyl)phenyl isocyanate
4-chloro-2-methoxyphenyl isocyanate
4-chloro-2-(trifluoroethyl)phenyl isocyanate
4-chloro-3-(trifluoromethyl)phenyl isocyanate
4-iodophenyl isocyanate
4-phenoxyphenyl isocyanate
4-ethoxyphenyl isocyanate
4-(methylthio)phenyl isocyanate
4-acetylphenyl isocyanate
4-isopropylphenyl isocyanate
4-ethylphenyl isocyanate
4-n-butylphenyl isocyanate
octyl isocyanate
2-naphthyl isocyanate
4-methyl-3-nitrophenyl isocyanate
4-chloro-2-nitrophenyl isocyanate
4-methyl-2-nitrophenyl isocyanate
2-fluoro-5-nitrophenyl isocyanate
2-methyl-5-nitrophenyl isocyanate
3-bromopropyl isocyanate
3-bromopropyl isocyanate
3-iodopropyl isocyanate
5-bromopentyl isocyanate
5-iodopentyl isocyanate
mesityl isocyanate
2-isopropyl-6-methylphenyl isocyanate
2,6-diethylphenyl isocyanate
5-chloro-o-tolyl isocyanate
4-chloro-2-methylphenyl isocyanate
4-(trifluoromethoxy)phenyl isocyanate
isobutylisocyanate
4-(trifluoromethylthio)phenyl isocyanate
2-chloro-5-(trifluoromethyl)phenyl isocyanate
2-chloro-6-methylphenyl isocyanate 2,4,5-trimethylphenylisocyanate
2-methyl-6-t-butylphenyl isocyanate
3-chloro-2-methoxyphenyl isocyanate
3-chloro-2-methylphenyl isocyanate
3-chloro-4-fluorophenyl isocyanate
4-cyanophenyl isocyanate
4-bromo-2-methylphenyl isocyanate
4-bromo-2,6-dimethylphenyl isocyanate
2,6-dibromo-4-fluorophenyl isocyanate
4-n-butoxyphenyl isocyanate
4-n-butoxycarbonylphenyl isocyanate
phenethyl isocyanate
2-methyl-3-nitrophenyl isocyanate
hexyl isocyanate
hexadecyl isocyanate
4-chloro-3-nitrophenyl isocyanate
2-chloro-4-nitrophenyl isocyanate
4,5-dimethyl-2-nitrophenyl isocyanate
2-chloro-5-nitrophenyl isocyanate
3-fluoro-4-methylphenyl isocyanate
5-fluoro-2-methylphenyl isocyanate
2-(methylthio)phenyl isocyanate
3-carbomethoxyphenyl isocyanate
2-biphenylyl isocyanate
4-isocyanato-biphenyl
4-(tert-butyl)phenylisocyanate
1-(4-bromophenyl)ethyl isocyanate
n-butyl isocyanatoacetate
dodecyl isocyanate
2,6-dichloropyrid-4-yl isocyanate
2-(thien-2-yl)ethyl isocyanate
2-bromo-4,6-difluorophenyl isocyanate
(R)-(+)-alpha-methylbenzyl isocyanate
1-(1-naphthyl)ethyl isocyanate
(S)-(+)-1-(1-naphthyl)ethyl isocyanate
3,4-difluorophenyl isocyanate
2-methoxy-5-nitrophenyl isocyanate
2-(chloromethyl)phenyl isocyanate
3-isopropenyl-alpha,alpha-dimethylbenzyl isocyanate
2-(trifluoromethoxy)phenyl isocyanate
4-(chloromethyl)phenyl isocyanate
1-adamantyl isocyanate
pentyl isocyanate
heptyl isocyanate
2-bromoethyl isocyanate
1,1,3,3-tetramethylbutyl isocyanate
3,5-dinitrophenyl isocyanate
4-(6-methyl-2-benzothiazolyl)phenyl isocyanate
2-iodophenyl isocyanate
2-n-propylphenyl isocyanate
4-benzyloxyphenyl isocyanate
2-phenoxyphenyl isocyanate
4-bromo-2-chlorophenyl isocyanate
4-bromo-2-fluorophenyl isocyanate
2-fluoro-5-methylphenyl isocyanate
4-fluoro-2-nitrophenyl isocyanate
2,3,4-trifluorophenyl isocyanate
4-heptyloxyphenyl isocyanate
4-dimethylaminophenyl isocyanate
2-(difluoromethoxy)phenyl isocyanate
4-(difluoromethoxy)phenyl isocyanate
3-(trifluoromethylthio)phenyl isocyanate
2-methylbenzyl isocyanate
3-methylbenzyl isocyanate
4-methylbenzyl isocyanate
2-chlorobenzyl isocyanate
4-fluorobenzyl isocyanate
3,4-dichorobenzyl isocyanate
4-methoxybenzyl isocyanate
2,6-difluorobenzoyl isocyanate
4-fluorobenzoyl isocyanate
2-fluoro-3-(trifluoromethyl)phenyl isocyanate
2-fluoro-5-(trifluoromethyl)phenyl isocyanate
2-fluoro-6-(trifluoromethyl)phenyl isocyanate
4-fluoro-2-(trifluoromethyl)phenyl isocyanate
4-fluoro-3-(trifluoromethyl)phenyl isocyanate
2-cyanophenyl isocyanate
3-cyclopentoxy-4-methoxyphenyl isocyanate
2-tert-butylphenyl isocyanate
4-n-butyl-2-methylphenyl isocyanate
2,6-dibromo-4-isopropylphenyl isocyanate
3-pyridyl isocyanate

EXAMPLE 11

Preparation of a Combinatorial Library of Tertiary Amino-triazole Compounds 420 resin bound amino triazoles are prepared as described in Example 7. Each of the 420 resin bound amino triazoles is then reacted with 132 different aldehydes to form the 55,440 member combinatorial library. The 132 aldehydes are as follows:

Paraformaldehyde
Acetaldehyde
Benzaldehyde
Butyraldehyde
Cinnamaldehyde trans
Cyclohexanecarboxaldehyde
Cyclopropanecarboxaldehyde
Diphenylacetaldehyde
Hydrocinnamaldehyde
Isobutyraldehyde
Isovaleraldehyde
1,3,5-Trimethylbenzaldehyde
Octyl aldehyde
Phenylacetaldehyde
Propionaldehyde
Trimethylacetaldehyde
Valeraldehyde
1,2,3,6-Tetrahydrobenzaldehyde
1,4- Benzodioxan-6-carboxaldehyde
1-Methyl-2-pyrrolecarboxaldehyde
1-Methylindole-3-carboxaldehyde
1-Naphthaldehyde 10-Chloro-9-anthraldehyde
2,3,4-Trifluorobenzaldehyde
2,3,5-Trichlorobenzaldehyde
2,3-(Methylenedioxy)benzaldehyde
2,3-Difluorobenzaldehyde
2,4,5-Trimethoxybenzaldehyde
2,4-Dichlorobenzaldehyde
3,5-Difluorobenzaldehyde
2,5-Dimethylbenzaldehyde
2,6-Difluorobenzaldehyde
2,6-Dimethoxybenzaldehyde
2-Bromobenzaldehyde
2-Chloro-6-fluorobenzaldehyde
2-Cyanobenzaldehyde
2-Ethylbutyraldehyde
2-Fluorobenzaldehyde
2-Furaldehyde
2-Methoxy-1-naphthaldehyde
2-Methoxybenzaldehyde
o-Anisaldehyde
2-Naphthaldehyde
2-Pyridinecarboxaldehyde
2-Quinolinecarboxaldehyde
2-Thiophenecarboxaldehyde
3,3-Dimethylbutyraldehyde
3,4-(Methylenedioxy)benzaldehyde
3,5,5-Trimethylhexanal
3,5-bis(Trifluoromethyl)benzaldehyde
3,5-Dibenzyloxybenzaldehyde
3,5-Dichlorobenzaldehyde
3,5-Dimethoxybenzaldehyde
3-(Trifluoromethyl)benzaldehyde
3-Fluoro-4-methoxybenzaldehyde
3-Fluoro-p-anisaldehyde
3-Fluorobenzaldehyde
3-Furaldehyde
3-Methoxybenzaldehyde
m-Anisaldehyde
3-Methyl-4-methoxybenzaldehyde
2-Methylbenzaldehyde
3-Methylbenzaldehyde
m-Tolualdehyde
3-Phenylbutyraldehyde
3-Pyridinecarboxaldehyde
3-Quinolinecarboxaldehyde
3-Thiophenearboxaldehyde
4-(Methylthio)benzaldehyde
4-(Trifluoromethyl)benzaldehyde
4-Acetamidobenzaldehyde
4-Methoxybenzaldehyde
4-Benzyloxybenzaldehyde
4-Biphenylcarboxaldehyde
4-Cyanobenzaldehyde
4-Fluorobenzaldehyde
4-Isopropylbenzaldehyde
4-Methoxy-1-naphthaldehyde 2,4-Dimethoxy-3-methylbenzaldehyde
4-Methyl benzaldehyde
p-Tolualdehyde
4-Propoxybenzaldehyde
4-Pyridinecarboxaldehyde
4-Quinolinecarboxaldehyde
5-Methyl-2-thiophenecarboxaldehyde
5-Methyl-2-furaldehyde
6-Methyl-2-pyridinecarboxaldehyde
Pyrrole-2-carboxaldehyde
2,4-Dimethoxybenzaldehyde
2,3,4-Trimethoxybenzaldehyde
2,2-Dimethyl-4-pentenal
3-Methoxy-2-nitrobenzaldehyde
2,5-Dimethoxybenzaldehyde
2-(4-Chlorophenylthio)benzaldehyde
2-Methylbutyraldehyde
2-Methylvaleraldehyde
2-Chlorobenzaldehyde
2-(Trifluoromethyl)benzaldehyde
2-Benzyloxy-3-methoxy-benzaldehyde
2-Phenylpropionaldehyde
3,4,5-Trimethoxybenzaldehyde
3-(Methylthio)propionaldehyde
3-Chloro-4-fluorobenzaldehyde
3-Chlorobenzaldehyde
3-Methoxy-4,5-methylenedioxybenzaldehyde
3-Methyl-2-butenal
4-(Diethylamino)benzaldehyde
4-(Trifluoromethoxy)benzaldehyde
4-Acetoxybenzaldehyde
4-Chlorobenzaldehyde
4-Pyrrolidinobenzaldehyde
5-Methylbenzo[b]thiophene-2-carboxaldehyde
Indole-3-carboxaldehyde
2-Fluoro-3-(trifluoromethyl)benzaldehyde
2-Thiazolecarboxaldehyde
4,5-Dimethyl-2-furaldehyde
4-tert-Butylbenzaldehyde
Phenanthrene-9-carboxaldehyde
5-(4-Chlorophenyl)furfural
3-Bromo-4-methoxybenzaldehyde
5-Ethyl-2-furaldehyde
5-Chloro-2-thiophenecarboxaldehyde
4-Ethylbenzaldehyde
2,4-Diethoxy-m-tolualdehyde
3-Methyl-2-thiophenecarboxaldehyde
4-Ethoxybenzaldehyde
2,6-Dimethyl-5-heptenal
2-Chloro-3,4-dimethoxybenzaldehyde
3,4-Diethoxybenzaldehyde
4-Chloro-3-fluorobenzaldehyde
3-Methyl-p-anisaldehyde
3-Methylbutyraldehyde

EXAMPLE 12

Cleavage and Extraction

To the dry resins (in tea bags or in wells of micrometer plates) containing the triazole compounds described in the above examples, appropriate amounts of TFA/DCA solution (20 to 50% TFA) were added. The mixtures were shaken for 2–5 hours at room temperature, dried under vacuum and the resins were then extracted with either $CH_3CN/H_2O$ (1:1) or AcOH. The extracts were lyophilized to give the cleaved triazoles and analyzed by mass spectrometry, as well as by HPLC equipped with a UV detector and an evaporative light scattering detector (ELSD).

EXAMPLE 13

Anti-microbial Screen

Streptococcus pyogenes (ATCC# 97-03 14289) are grown in Todd Hewitt Broth (THB) (Difco Laboratories #0492-17-6) overnight until they reach an optical density of ( OD=0.636@ 570 nm) by reading 0.1 ml in a 96 well microtiter plate in a Molecular Devices Thermomax. This preparation is kept frozen as stocks in 30% v/v glycerol in 1.5 ml aliquots at −70° C. until use. Prior to screening, 1.5 ml aliquots are thawed and diluted into 50 ml THB. 200 ul of this dilution is added to 92 wells of microtiter plate. To three wells THB (200 ul) is added to serve as a blank and a sterility control. Test compounds in DMSO and appropriate concentrations of DMSO are added to Growth/Solvent Controls at 0 time. Plates are read at 0 time at 570 nm in the Molecular Devices plate reader to obtain compounds correction factors for insoluble or colored compounds. Plates are read again at 4 hrs.

Compounds are assayed at a concentration of 170 µg/ml. Percent inhibition for each compound is calculated using the following formulae:

Color correct=(O.D. 0 hr−Blank 0 hr)−(Solvent Control 0 hr−Blank 0 hr)

% Inhibition=100−(O.D.test compound 4hr−Blank 4 hr−color correct) divided by (O.D.growth/solvent control 4 hr−Blank 4 hr)

Although the invention has been described with reference to the examples provided above, it should be understood that various modifications can be made by those skilled in the art without departing from the invention. Accordingly, the invention is set out in the following claims.

We claim:
1. A single triazole compound of the formula:

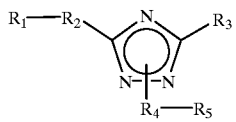

wherein:
$R_1$ is selected from the group consisting of —NHC(O)NR$_6$R$_7$, —CO$_2$R$_6$, —OR$_6$, —NR$_6$R$_7$, —C(O)NR$_6$R$_7$, and —CH$_2$NR$_6$R$_7$, wherein R$_6$ is a hydrogen atom or a functionalized resin, and R$_7$ is selcted from the group consisting of a hydrogen atom, $C_1$ to $C_6$ alkyl, $C_1$ to $C_6$ substituted alkyl, $C_2$ to $C_7$ alkenyl, $C_2$ to $C_7$ substituted alkenyl, phenyl, substituted phenyl, naphthyl, substituted naphthyl, $C_7$ to $C_{12}$ phenylalkyl, $C_7$ to $C_{12}$ substituted phenylalkyl, heteroaryl, substituted heteroaryl, heterocycle and substituted heterocycle;

$R_2$ is selected from the group consisting of $C_1$ to $C_{12}$ alkylene, $C_1$ to $C_{12}$ substituted alkylene, $C_2$ to $C_7$ alkenylene, $C_2$ to $C_7$ substituted alkenylene, $C_2$ to $C_7$ alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, phenylene, substituted phenylene, naphthylene, substituted naphthylene, heterocyclene, substituted heterocyclene, heteroarylene, substituted heteroarylene, $C_7$ to $C_{12}$ phenylalkoxy, $C_7$ to $C_{12}$ substituted phenylalkoxy, the formula:

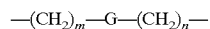

wherein m and n are integers independently selected from 0 to 6, provided that m and n are not together 0; and G is selected from phenylene and substituted phenylene, the formula:

wherein m and n are integers independently selected from 0 to 6, provided that m and n are not together 0; and X is selected from the group consisting of a hydrogen atom, $C_1$ to $C_6$ alkyl, $C_1$ to $C_6$ substituted alkyl, $C_1$ to $C_7$ acyl, $C_1$ to $C_7$ substituted acyl, $C_1$ to $C_4$ alkyl sulfonyl, $C_1$ to $C_4$ substituted alkyl sulfonyl, phenylsulfonyl, substituted phenylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl, substituted phenylaminothiocarbonyl, $C_1$ to $C_7$ alkoxycarbonyl, $C_1$ to $C_7$ substituted alkoxycarbonyl, phenoxycarbonyl and substituted phenoxycarbonyl, the formula:

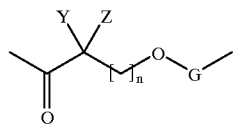

wherein n is an integer selected from 0 to 6; Y and Z are together or independently a hydrogen atom, $C_6$ to $C_1$ alkyl, $C_1$ to $C_6$ substituted alkyl, $C_2$ to $C_7$ alkenyl, $C_2$ to $C_7$ alkynyl, $C_2$ to $C_7$ substituted alkenyl, $C_2$ to $C_7$ substituted alkynyl, $C_1$ to $C_7$ acyl, $C_1$ to $C_7$ substituted acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl and protected hydroxymethyl; and G is selected from phenylene and substituted phenylene, and the formula:

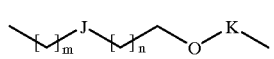

(III)

wherein J and K are each selected from the group consisting of phenylene and substituted phenylene, and m and n are independently selected from 0 and 1;

$R_3$ is selected from the group consisting of a hydrogen atom, $C_1$ to $C_6$ alkyl, $C_1$ to $C_6$ substituted alkyl, phenyl, substituted phenyl, heteroaryl, substituted heteroaryl, carboxy, protected carboxy, cyano, (monosubstituted) amino, protected (monosubstituted)amino, (disubstituted)amino, $C_1$ to $C_7$ acyl, $C_1$ to $C_7$ substituted acyl, $C_1$ to $C_7$ alkoxycarbonyl, $C_1$ to $C_7$ substituted alkoxycarbonyl, $C_1$ to $C_7$ alkylaminocarbonyl, $C_1$ to $C_7$ substituted alkylaminocarbonyl, phenylaminocarbonyl, substituted phenylaminocarbonyl, heterocycle, substituted heterocycle, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl;

$R_4$ is selected from the group consisting of the formula:

—D-phenylene-E— wherein:

D is directly attached to the triazole ring and D and E are independently selected from the group consisting of $C_1$ to $C_6$ alkylene, $C_2$ to $C_7$ alkenylene, $C_2$ to $C_7$ alkynylene, $C_1$ to $C_6$ substituted alkylene, $C_2$ to $C_7$ substituted alkenylene, $C_2$ to $C_7$ substituted alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, $C_7$ to $C_{12}$ phenylalkylene, $C_7$ to $C_{12}$ substituted phenylalkylene, —$R_{10}$—O—$R_{11}$—, —$NR_{10}R_{11}$—, —$R_{10}$—NH—$R_{11}$— and —C(O)$NR_{10}R_{11}$—, wherein $R_{10}$ and $R_{11}$ are independently absent or present and selected from the group consisting of $C_1$ to $C_6$ alkylene, $C_1$ to $C_6$ substituted alkylene, $C_7$ to $C_{12}$ phenylalkylene and $C_7$ to $C_{12}$ substituted phenylalkylene, provided that, when D is —$NR_{10}R_{11}$— or —C(O)$NR_{10}R_{11}$—, $R_{11}$ is present and directly connected to the triazole ring;

the formula:

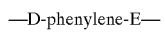

wherein:

$R_8$ and $R_9$ are together or independently selected from the group consisting of a hydrogen atom, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ acyl, $C_1$ $C_7$ substituted acyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino and amino-protecting group; and m and n are independently 0, 1, 2, 3 or 4; and and the formulae:

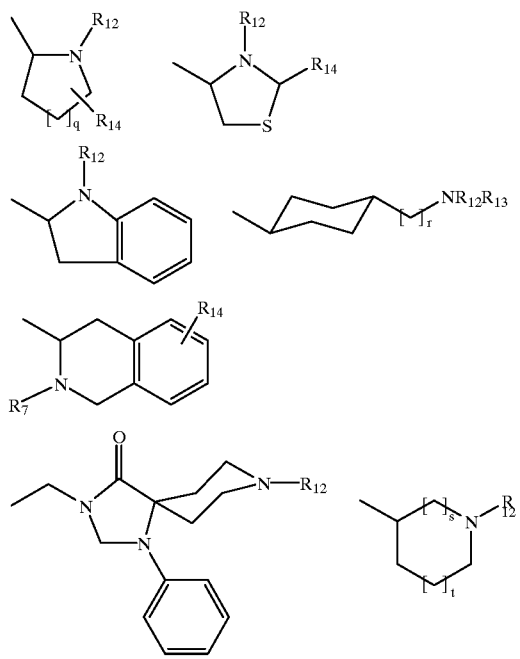

wherein q is selected from 1 and 2; r is is selected from 0 and 1; s and t are independently selected from 0, 1 and 2; and $R_{12}$ and $R_{13}$ are independently selected from the group consisting of a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl; and $R_{14}$ is selected from a hydrogen atom, —OH, hydroxyprotecting group, $C_1$ to $C_6$ alkyl, $C_1$ to $C_6$ substituted alkyl, $C_1$ to $C_7$ alkoxy, $C_1$ to $C_7$ phenylalkoxy, phenyl, substituted phenyl, heteroaryl and substituted heteroaryl; and $R_5$ is absent or is selected from the group consisting of a hydrogen atom, a halide, —OH, —$CO_2H$, —CHO, —$CO_2R_{15}$, —C(O)$NR_{15}R_{16}$ and —$NR_{15}R_{16}$, wherein $R_{15}$ and $R_{16}$ are independently selected from a hydrogen atom, $C_1$ to $C_6$ alkyl, $C_1$ to $C_6$ substituted alkyl, phenyl, substituted phenyl, heterocycle, substituted heterocycle, heteroaryl, substituted heteroaryl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, $C_7$ to $C_{12}$ phenylalkyl, $C_7$ to $C_{12}$ substituted phenylalkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl, and the formulae:

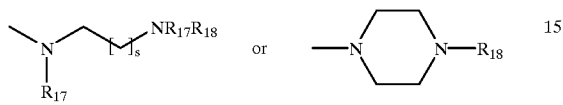

wherein $R_{17}$ and $R_{18}$ are independently selected from a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl; and s is an integer selected from 1 to 5;

provided that, when (1) $R_8$ and $R_9$ are both hydrogen atoms; or (2) one of $R_8$ and $R_9$ is a hydrogen atom and the other is a $C_1$ to $C_6$ alkyl or $C_1$ to $C_6$ substituted alkyl where the substitution is one or more halides, $R_5$ is not a hydrogen atom or a halide; and provided that, when one of $R_8$ and $R_9$ is a hydrogen atom and the other is a $C_2$ to $C_7$ alkenyl, $R_5$ is not a hydrogen atom; or a pharmaceutically acceptable salt of a compound thereof.

2. A single triazole compound of claim 1, wherein $R_1$ is selected from the group consisting of —NHC(O)NR_6R_7, —OR_6, —C(O)NR_6R_7, and —CH_2NR_6R_7, wherein $R_6$ is a hydrogen atom or a functionalized resin, and $R_7$ is a hydrogen atom, $C_1$ to $C_6$ alkyl, $C_1$ to $C_6$ substituted alkyl, $C_2$ to $C_7$ alkenyl, $C_2$ to $C_7$ substituted alkenyl, phenyl, substituted phenyl, naphthyl, substituted naphthyl, $C_7$ to $C_{12}$ phenylalkyl, $C_7$ to $C_{12}$ substituted phenylalkyl, heteroaryl, substituted heteroaryl, heterocycle and substituted heterocycle.

3. A single triazole compound of claim 1, wherein $R_2$ is selected from the group consisting of $C_1$ to $C_{12}$ alkylene, $C_1$ to $C_{12}$ substituted alkylene, $C_2$ to $C_7$ alkenylene, $C_2$ to $C_7$ substituted alkenylene, $C_2$ to $C_7$ alkynylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, phenylene, substituted phenylene, naphthylene, substituted naphthylene, $C_7$ to $C_{12}$ phenylalkoxy, $C_7$ to $C_{12}$ substituted phenylalkoxy, and the formula:

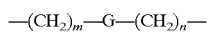

wherein m and n are integers independently selected from 0 to 6, provided that m and n are not together 0; and G is selected from phenylene and substituted phenylene.

4. A single triazole compound of claim 1, wherein $R_3$ is selected from the group consisting of $C_1$ to $C_6$ alkyl, $C_1$ to $C_6$ substituted alkyl, phenyl, substituted phenyl, heteroaryl, substituted heteroaryl, heterocycle, substituted heterocycle, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl.

5. A single triazole compound of claim 1, wherein $R_4$ is selected from the group consisting of the formula:

—D-phenylene-E— wherein:

D is directly attached to the triazole ring and D and E are independently selected from the group consisting of $C_1$ to $C_6$ alkylene, $C_2$ to $C_7$ alkenylene, $C_2$ to $C_7$ alkynylene, $C_1$ to $C_6$ substituted alkylene, $C_2$ to $C_7$ substituted alkenylene, $C_2$ to $C_7$ substituted alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, $C_7$ to $C_{12}$ phenylalkylene, $C_7$ to $C_{12}$ substituted phenylalkylene, —$R_{10}$—O—$R_{11}$—, —$NR_{10}R_{11}$—, —$R_{10}$—NH—$R_{11}$— and —$C(O)NR_{10}R_{11}$—, wherein $R_{10}$ and $R_{11}$ are independently absent or present and selected from the group consisting of $C_1$ to $C_6$ alkylene, $C_1$ to $C_6$ substituted alkylene, $C_7$ to $C_{12}$ phenylalkylene and $C_7$ to $C_{12}$ substituted phenylalkylene, provided that, when D is —$NR_{10}R_{11}$— or —$C(O)NR_{10}R_{11}$—, $R_{11}$ is present and directly connected to the triazole ring;

and the formula:

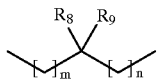

wherein:

$R_8$ and $R_9$ are together or independently slected from the group consisting of a hydrogen atom, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ acyl, $C_1$ $C_7$ substituted acyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino and amino-protecting group; and m and n are independently 0, 1, 2, 3 or 4.

6. A single triazole compound of claim 1, wherein $R_5$ is absent or is selected from the group consisting of a hydrogen atom, a halide, —OH, —$CO_2H$, —CHO, —$C(O)NR_{15}R_{16}$ and —$NR_{15}R_{16}$, wherein $R_{15}$ and $R_{16}$ are independently selected from a hydrogen atom, $C_1$ to $C_6$ alkyl, $C_1$ to $C_6$ substituted alkyl, phenyl, substituted phenyl, heterocycle, substituted heterocycle, heteroaryl, substituted heteroaryl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, $C_7$ to $C_{12}$ phenylalkyl and $C_7$ to $C_{12}$ substituted phenylalkyl; or $R_5$ is —$NR_{15}R_{16}$, wherein $R_{15}$ and $R_{16}$ are independently selected from $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl.

7. A single triazole compound of claim 1, wherein $R_1$ is selected from the group consisting of —NHC(O)$NR_6R_7$, —$OR_6$, —C(O)$NR_6R_7$, and —$CH_2NR_6R_7$, wherein $R_6$ is a hydrogen atom or a functionalized resin, and $R_7$ is a hydrogen atom, $C_1$ to $C_6$ alkyl, $C_1$ to $C_6$ substituted alkyl, $C_2$ to $C_7$ alkenyl, $C_2$ to $C_7$ substituted alkenyl, phenyl, substituted phenyl, naphthyl, substituted naphthyl, $C_7$ to $C_{12}$ phenylalkyl, $C_7$ to $C_{12}$ substituted phenylalkyl, heteroaryl, substituted heteroaryl, heterocycle and substituted heterocycle;

$R_2$ is selected from the group consisting of $C_1$ to $C_{12}$ alkylene, $C_1$ to $C_{12}$ substituted alkylene, $C_2$ to $C_7$ alkenylene, $C_2$ to $C_7$ substituted alkenylene, $C_2$ to $C_7$ alkynylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, phenylene, substituted phenylene, naphthylene, substituted naphthylene, $C_7$ to $C_{12}$ phenylalkoxy, $C_7$ to $C_{12}$ substituted phenylalkoxy, and the formula:

wherein m and n are integers independently selected from 0 to 6, provided that m and n are not together 0; and G is selected from phenylene and substituted phenylene;

$R_3$ is selected from the group consisting of $C_1$ to $C_6$ alkyl, $C_1$ to $C_6$ substituted alkyl, phenyl, substituted phenyl, heteroaryl, substituted heteroaryl, heterocycle, substituted heterocycle, naphthyl, substituted naphthyl, $C_5$ to $C_7$ cycloalkyl, $C_5$ to $C_7$ substituted cycloalkyl, $C_5$ to $C_7$ cycloalkenyl and $C_5$ to $C_7$ substituted cycloalkenyl;

$R_4$ is selected from the group consisting of the formula:

—D-phenylene-E— wherein:

D is directly attached to the triazole ring and D and E are independently selected from the group consisting of $C_1$ to $C_6$ alkylene, $C_2$ to $C_7$ alkenylene, $C_2$ to $C_7$ alkynylene, $C_1$ to $C_6$ substituted alkylene, $C_2$ to $C_7$ substituted alkenylene, $C_2$ to $C_7$ substituted alkynylene, $C_5$ to $C_7$ cycloalkylene, $C_5$ to $C_7$ substituted cycloalkylene, $C_5$ to $C_7$ cycloalkenylene, $C_5$ to $C_7$ substituted cycloalkenylene, $C_7$ to $C_{12}$ phenylalkylene, $C_7$ to $C_{12}$ substituted phenylalkylene, —$R_{10}$—O—$R_{11}$—, —$NR_{10}R_{11}$—, —$R_{10}$—NH—$R_{11}$— and —C(O)$NR_{10}R_{11}$—, wherein $R_{10}$ and $R_{11}$ are independently absent or present and selected from the group consisting of $C_1$ to $C_6$ alkylene, $C_1$ to $C_6$ substituted alkylene, $C_7$ to $C_{12}$ phenylalkylene and $C_7$ to $C_{12}$ substituted phenylalkylene, provided that, when D is —$NR_{10}R_{11}$— or —C(O)$NR_{10}R_{11}$—, $R_{11}$ is present and directly connected to the triazole ring;

and the formula:

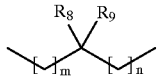

wherein:

$R_8$ and $R_9$ are together or independently slected from the group consisting of a hydrogen atom, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ acyl, $C_1$ $C_7$ substituted acyl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, a heterocyclic ring, substituted heterocyclic ring, heteroaryl, substituted heteroaryl, $C_7$ to $C_{12}$ phenylalkyl, $C_7$ to $C_{12}$ substituted phenylalkyl, $C_7$ to $C_{12}$ phenylalkoxy, $C_7$ to $C_{12}$ substituted phenylalkoxy, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino and amino-protecting group; and m and n are independently 0, 1, 2, 3 or 4; and $R_5$ is absent or is selected from the group consisting of a hydrogen atom, a halide, —OH, —$CO_2H$, —CHO, —C(O)$NR_{15}R_{16}$ and —$NR_{15}R_{16}$, wherein $R_{15}$ and $R_{16}$ are independendently selected from a hydrogen atom, $C_1$ to $C_6$ alkyl, $C_1$ to $C_6$ substituted alkyl, phenyl, substituted phenyl, heterocycle, substituted heterocycle, heteroaryl, substituted heteroaryl, $C_5$ to $C_7$ cycloalkyl, $C_5$ to $C_7$ substituted cycloalkyl, $C_5$ to $C_7$ cycloalkenyl, $C_5$ to $C_7$ substituted cycloalkenyl, $C_7$ to $C_{12}$ phenylalkyl and $C_7$ to $C_{12}$ substituted phenylalkyl; or $R_5$ is —$NR_{15}R_{16}$, wherein $R_{15}$ and $R_{16}$ are independently selected from $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl, $C_1$ to $C_6$ alkylaminothiocarbonyl, $C_1$ to $C_6$ substituted alkylaminothiocarbonyl, phenylaminothiocarbonyl and substituted phenylaminothiocarbonyl.

8. A single triazole compound of claim 1, wherein:

$R_1$ combined with $R_2$ is selected from the group consisting of 4-hydroxyphenyl, 3-chloro-4-hydroxyphenyl, 3-methoxy-4-hydroxyphenyl and 3-hydroxyphenyl;

$R_3$ is selected from the group consisting of 4-methylphenyl, phenyl, 4-chlorophenyl, 3-nitrophenyl and 4-pyridino;

$R_4$ is selected from the group consisting of ethylene, hexamethylene, 2-methylpropylene, -4-($CH_2CH_2O$)$C_6H_4CH_2$— and -4-($CH_2CH_2N(CH_2CH_3)$)$C_6H_4CH_2$—; and $R_5$ is —$NR_{15}R_{16}$, wherein $R_{15}$ is a hydrogen atom; and $R_{16}$ is selected from the group consisting of cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, 1,4-piperazino-bispropyl, L-1-(ethoxycarbonyl)ethyl, 4-aminocyclohexyl, 3,3-dimethylbutyl and methoxycarbonylmethyl.

9. A single triazole compound of claim 1, wherein:

$R_1$ combined with $R_2$ is selected from the group consisting of 4-hydroxyphenyl, 3-chloro-4-hydroxyphenyl, 3-methoxy-4-hydroxyphenyl and 3-hydroxyphenyl;

$R_3$ is selected from the group consisting of 4-methylphenyl, phenyl, 4-chlorophenyl, 3-nitrophenyl and 4-pyridino;

$R_4$ is selected from the group consisting of ethylene, hexamethylene, 2-methylpropylene, -4-($CH_2CH_2O$)$C_6H_4CH_2$— and -4-($CH_2CH_2N(CH_2CH_3)$)$C_6H_4CH_2$—; and $R_5$ is —$NR_{15}R_{16}$, wherein $R_{15}$ is selected from the group consisting of cyclobutanecarbonyl, 2-pyrazinecarbonyl, benzyloxyacetyl, 1-acetylpiperidine-4-carbonyl, 3,4-dimethoxybenzoyl, 2-fluoro-5-nitrobenzoyl, 2-chloro-5-(methylthio)benzoyl, 6-methylchromone-2-carbonyl, 2-methylcyclopropanecarbonyl, pyridine-3-carbonyl, (R)(-)α-methoxyphenylacetyl, 4-(dimethylamino)butyryl, 3-methoxybenzoyl, 4-chloro-3-nitrobenzoyl, 4-(methylthio)benzoyl, benzofuran-2-carbonyl, 2,2,3,3-tetramethylcyclopropanecarbonyl, 6-methylpyridine-3-carbonyl, 4-(methoxycarbonyl)benzoyl, L-2-pyrrolidone-5-carbonyl, piperonyloyl, 4-methoxy-3-nitrobenzoyl, 2-(methylthio)pyridine-3-carbonyl, 7-methoxy-2-benzofurancarbonyl, 4-methylpentanoyl, 6-hydroxy-pyridine-2-carbonyl, benzoyl, acetamidoacetyl, 4-phenoxybenzoyl, 4-nitrobenzoyl, 3,4-dichlorobenzoyl, 2-furancarbonyl, cyclopropanecarbonyl, 6-chloropyridine-3-carbonyl, 4-methylbenzoyl, 3-methylbutyryl, 3-phenoxybenzoyl, 3-methyl-4-nitrobenzoyl, 2-methoxy-4-(methylthio)-benzoyl, 3-methylbenzoyl, 3,5,5-trimethylhexanoyl, 5-bromo-pyridine-3-carbonyl, hydrocinnamoyl, cyclohexanepropionyl, 4-chloro-2-methoxybenzoyl, 2-fluorobenzoyl, 4-propylbenzoyl, 4-cyanobenzoyl, cyclopentylacetyl, 4-methoxy-2-quinolinecarbonyl, 4-isopropylbenzoyl, 4-pentenoyl, (3,4-dimethoxyphenyl)acetyl, 2,6-difluorobenzoyl, (phenylthio)acetyl, 3-cyanobenzoyl, octanoyl, 2-(allylthio)pyridine-3-carbonyl, p-tolylacetyl, 2-norbornaneacetyl, 4-ethoxyphenylacetyl, 3-nitrophenylacetyl, 4-pentylbenzoyl, 4-azidobenzoyl, 3-pyridinepropionyl, 1-naphthylacetyl, 4-carbonyl-1-(furfuryl)pyrrolidin-2-one, benzoylformyl, 4-fluorophenylacetyl, 4-cyclohexylbenzoyl, 3-benzoylpropionyl, acetyl, 3,4-dichlorophenylacetyl, α-methylcinnamoyl, cyclohexylidenecyanoacetyl, phenoxyacetyl, 2-chloro-4-fluorophenylacetyl, trans-2-phenyl-1-cyclopropanecarbonyl, 4-biphenylacetyl, trans-3-hexenoyl, 3-(trifluoromethyl)phenylacetyl, 4-bromophenylacetyl, tetrahydro-2-furoyl, 4-phenoxybutyryl, phthalimidoacetyl, 4-isopropylcinnamoyl, 3-methylindene-2-carbonyl, methoxyacetyl, 2-thiopheneacetyl, ethoxyacetyl, 2-ethyl-2-hexenoyl, 2-(2-(2-methoxyethoxy)ethoxy)acetyl, 3,4-dihydro-2,2-dimethyl-4-oxo-2H-pyran-6-carbonyl, (methylthio)acetyl and diethylphosphonoacetyl; and $R_{16}$ is selected from the group consisting of cyclopentyl, heptyl, 4-fluorobenzyl, 3-imidazolopropyl, 3-chlorobenzyl, 3-(N-methyl-N-(3-aminopropyl)amino)propyl, 2,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, L-1-(ethoxycarbonyl)ethyl, 4-aminocyclohexyl, 3,3-dimethylbutyl and methoxycarbonylmethyl.

10. A single triazole compound of claim 1, wherein:

$R_1$ combined with $R_2$ is selected from the group consisting of 4-hydroxyphenyl, 3-chloro-4-hydroxyphenyl, 3-methoxy-4-hydroxyphenyl and 3-hydroxyphenyl;

$R_3$ is selected from the group consisting of 4-methylphenyl, phenyl, 4-chlorophenyl, 3-nitrophenyl and 4-pyridino;

$R_4$ is selected from the group consisting of ethylene, hexamethylene, 2-methylpropylene, -4-($CH_2CH_2O$)$C_6H_4CH_2$— and -4-($CH_2CH_2N(CH_2CH_3)$)$C_6H_4CH_2$—; and $R_5$ is —$NR_{15}R_{16}$, wherein $R_{15}$ is selected from the group consisting of 2-mesitylenesulfonyl, 2-naphthalenesulfonyl, 2-thiophenesulfonyl, 4-methoxybenzenesulfonyl, benzenesulfonyl, 4-acetamidobenzenesulfonyl, p-toluenesulfonyl, 3,4-dimethoxybenzenesulfonyl, 3-chloro-4-fluorobenzenesulfonyl, 3-(trifluoromethyl)benzenesulfonyl, 4-ethylbenzenesulfonyl, 2-chloro-6-methylbenzenesulfonyl, 3,5-dichlorobenzenesulfonyl, 3-chlorobenzenesulfonyl, 3-fluorobenzenesulfonyl, 5-chloro-1,3-dimethylpyrazole-4-sulphonyl, 3,5-dimethylisoxazole-4-sulfonyl, 2-methoxycarbonylthiophene-3-sulphonyl, 5-chloro-2-methoxybenzenesulfonyl, 4-cyanobenzenesulfonyl, 3-cyanobenzenesulphonyl, 3-chloro-4-methylbenzenesulphonyl, 2,4-difluorobenzenesulfonyl, 2-fluorobenzenesulfonyl, 4-isopropylbenzenesulfonyl, 2,5-dimethoxybenzenesulfonyl, 3,4-dichlorobenzenesulfonyl, 2,3,5,6-tetramethylbenzenesulfonyl, 2-chlorobenzenesulfonyl, 3-nitrobenzenesulfonyl, 4-acetylbenzenesulfonyl, 4-methyl-3-nitrobenzenesulfonyl, 4-n-butylbenzenesulfonyl, 4-nitrobenzenesulfonyl, 4-propylbenzenesulfonyl, 5-fluoro-2-methylbenzenesulfonyl, β-styrenesulfonyl, 4-chloro-2,5-dimethylbenzenesulphonyl, m-toluenesulfonyl and p-xylene-2-sulfonyl; and $R_{16}$ is selected from the group consisting of cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-aminooctyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, L-1-(ethoxycarbonyl)ethyl, 4-aminocyclohexyl, 3,3-dimethylbutyl and methoxycarbonylmethyl.

11. A single triazole compound of claim 1, wherein:

$R_1$ combined with $R_2$ is selected from the group consisting of 4-hydroxyphenyl, 3-chloro-4-hydroxyphenyl, 3-methoxy-4-hydroxyphenyl and 3-hydroxyphenyl;

$R_3$ is selected from the group consisting of 4-methylphenyl, phenyl, 4-chlorophenyl, 3-nitrophenyl and 4-pyridino;

$R_4$ is selected from the group consisting of ethylene, hexamethylene, 2-methylpropylene, -4-$(CH_2CH_2O)C_6H_4CH_2$— and -4-$(CH_2CH_2N(CH_2CH_3))C_6H_4CH_2$—; and $R_5$ is —$NR_{15}R_{16}$, wherein $R_{15}$ is selected from the group consisting of trans-2-phenylcyclopropylaminocarbonyl, phenylaminocarbonyl, 2-bromophenylaminocarbonyl, 2-fluorophenylaminocarbonyl, 2,4-difluorophenylaminocarbonyl, 2,6-difluorophenylaminocarbonyl, 2-chlorophenylaminocarbonyl, 2,3-dichlorophenylaminocarbonyl, 2,4-dichlorophenylaminocarbonyl, 2,5-dichlorophenylaminocarbonyl, 2,6-dichlorophenylaminocarbonyl, 2-methoxyphenylaminocarbonyl, 2,4-dimethoxyphenylaminocarbonyl, 2,5-dimethoxyphenylaminocarbonyl, 2-ethoxyphenylaminocarbonyl, 2-(trifluoromethyl)phenylaminocarbonyl, o-tolylaminocarbonyl, 2,6-dimethylphenylaminocarbonyl, 2-ethylphenylaminocarbonyl, 3-bromophenylaminocarbonyl, 3-fluorophenylaminocarbonyl, 2-chlorophenylaminocarbonyl, 3,4-dichlorophenylaminocarbonyl, 3-methoxyphenylaminocarbonyl, 3-(trifluoromethyl)phenylaminocarbonyl, m-tolylaminocarbonyl, 4-bromophenylaminocarbonyl, 4-fluorophenylaminocarbonyl, 4-chlorophenylaminocarbonyl, 4-methoxyphenylaminocarbonyl, 4-(ethoxycarbonyl)phenylaminocarbonyl, 4-(trifluoromethyl)phenylaminocarbonyl, p-tolylaminocarbonyl, benzoylaminocarbonyl, trichloroacetylaminocarbonyl, chloroacetylaminocarbonyl, t-butylaminocarbonyl, (S)-(−)-alpha-methylbenzylaminocarbonyl, isopropylaminocarbonyl, methylaminocarbonyl, octadeylaminocarbonyl, ethylaminocarbonyl, 2-chloroethylaminocarbonyl, allylaminocarbonyl, n-propylaminocarbonyl, n-butylaminocarbonyl, cyclohexylaminocarbonyl, 1-naphthylaminocarbonyl, (R)-(−)-1-(1-naphthyl)ethylaminocarbonyl, 4-fluoro-3-nitrophenylaminocarbonyl, 2-nitrophenylaminocarbonyl, 3-nitrophenylaminocarbonyl, 4-nitrophenylaminocarbonyl, 2,6-diisopropylphenylaminocarbonyl, benzylaminocarbonyl, trichloromethylaminocarbonyl, 3-chloropropylaminocarbonyl, ethoxycarbonylaminocarbonyl, 3,5-bis(trifluoromethyl)-phenylaminocarbonyl, 2,5-difluorophenylaminocarbonyl, 2,4,5-trichlorophenylaminocarbonyl, 2,4,6-trichlorophenylaminocarbonyl, 2-(methoxycarbonyl)phenylaminocarbonyl, 2-(ethoxycarbonyl)phenylaminocarbonyl, 2-isopropylphenylaminocarbonyl, 2,3-dimethylphenylaminocarbonyl, 4-methoxy-2-methylphenylaminocarbonyl, 2,4-dimethylphenylaminocarbonyl, 2,5-dimethylphenylaminocarbonyl, 2-ethyl-6-methylphenylaminocarbonyl, 3-cyanophenylaminocarbonyl, 5-chloro-2,4-dimethoxyphenylaminocarbonyl, 3-chloro-4-methylphenylaminocarbonyl, 3,5-dichlorophenylaminocarbonyl, 2-methoxy-5-chlorophenylaminocarbonyl, 3,4,5-trimethoxyphenylaminocarbonyl, 3,5-dimethoxyphenylaminocarbonyl, 3-(methylthio)phenylaminocarbonyl, 3-(ethoxycarbonyl)phenylaminocarbonyl, 3-acetylphenylaminocarbonyl, 3,4-dimethylphenylaminocarbonyl, 3,5-dimethylphenylaminocarbonyl, 2-methoxy-5-methylphenylaminocarbonyl, 3-ethylphenylaminocarbonyl, 4-bromo-2-(trifluoromethyl)-phenylaminocarbonyl, 4-chloro-2-methoxyphenylaminocarbonyl, 4-chloro-2-(trifluoromethyl)-phenylaminocarbonyl, 4-chloro-3-(trifluoromethyl)-phenylaminocarbonyl, 4-iodophenylaminocarbonyl, 4-phenoxyphenylaminocarbonyl, 4-ethoxyphenylaminocarbonyl, 4-(methylthio)phenylaminocarbonyl, 4-acetylphenylaminocarbonyl, 4-isopropylphenylaminocarbonyl, 4-ethylphenylaminocarbonyl, 4-n-butylphenylaminocarbonyl, octylaminocarbonyl, 2-naphthylaminocarbonyl, 4-methyl-3-nitrophenylaminocarbonyl, 4-chloro-2-nitrophenylaminocarbonyl, 4-methyl-2-nitrophenylaminocarbonyl, 2-fluoro-5-nitrophenylaminocarbonyl, 2-methyl-5-nitrophenylaminocarbonyl, 3-bromopropylaminocarbonyl, 3-iodopropylaminocarbonyl, 5-bromopentylaminocarbonyl, 5-iodopentylaminocarbonyl, mesitylaminocarbonyl, 2-isopropyl-6-methylphenylaminocarbonyl, 2,6-diethylphenylaminocarbonyl, 5-chloro-o-tolylaminocarbonyl, 4-chloro-2-methylphenylaminocarbonyl, 4-(trifluoromethoxy)phenylaminocarbonyl, isobutylaminocarbonyl, 4-(trifluoromethylthio)-phenylaminocarbonyl, 2-chloro-5-(trifluoromethyl)-phenylaminocarbonyl, 2-chloro-6-methylphenylaminocarbonyl, 2,4,5-trimethylphenylaminocarbonyl, 2-methyl-6-t-butylphenylaminocarbonyl, 3-chloro-2-methoxyphenylaminocarbonyl, 3-chloro-2-methylphenylaminocarbonyl, 3-chloro-4-fluorophenylaminocarbonyl, 4-cyanophenylaminocarbonyl, 4-bromo-2-methylphenylaminocarbonyl, 4-bromo-2,6-dimethylphenylaminocarbonyl, 2,6-dibromo-4-fluorophenylaminocarbonyl, 4-n-butoxyphenylaminocarbonyl, 4-n-butoxycarbonylphenylaminocarbonyl, phenethylaminocarbonyl, 2-methyl-3-nitrophenylaminocarbonyl, hexylaminocarbonyl, hexadecylaminocarbonyl, 4-chloro-3-nitrophenylaminocarbonyl, 2-chloro-4-nitrophenylaminocarbonyl, 4,5-dimethyl-2-nitrophenylaminocarbonyl, 2-chloro-5-nitrophenylaminocarbonyl, 3-fluoro-4-methylphenylaminocarbonyl, 5-fluoro-2-methylphenylaminocarbonyl, 2-(methylthio)phenylaminocarbonyl, 3-carbomethoxyphenylaminocarbonyl, 2-biphenylylaminocarbonyl, 4-biphenylaminocarbonyl, 4-(t-butyl)phenylaminocarbonyl, 1-(4-bromophenyl)ethylaminocarbonyl, n-butoxycarbonylmethylaminocarbonyl, dodecylaminocarbonyl, 2,6-dichloropyrid-4-ylaminocarbonyl, 2-(thien-2-yl)ethylaminocarbonyl, 2-bromo-4,6-difluorophenylaminocarbonyl, (R)-(+)-α-methylbenzylaminocarbonyl, 1-(1-naphthyl)ethylaminocarbonyl, (S)-(+)-1-(1-naphthyl)ethylaminocarbonyl, 3,4-difluorophenylaminocarbonyl, 2-methoxy-5-nitrophenylaminocarbonyl, 2-(chloromethyl)phenylaminocarbonyl, 3-isopropenyl-α,α-dimethylbenzylaminocarbonyl, 2-(trifluoromethoxy)phenylaminocarbonyl, 4-(chloromethyl)phenylaminocarbonyl, 1-adamantylaminocarbonyl, pentylaminocarbonyl, heptylaminocarbonyl, 2-bromoethylaminocarbonyl, 1,1,3,3-tetramethylbutylaminocarbonyl, 3,5-dinitrophenylaminocarbonyl, 4-(6-methyl-2-benzothiazolyl)-phenylaminocarbonyl, 2-iodophenylaminocarbonyl, 2-n-propylphenylaminocarbonyl, 4-benzyloxyphenylaminocarbonyl, 2-phenoxyphenylaminocarbonyl, 4-bromo-2-chlorophenylaminocarbonyl, 4-bromo-2-fluorophenylaminocarbonyl, 2-fluoro-5-methylphenylaminocarbonyl, 4-fluoro-2-nitrophenylaminocarbonyl, 2,3,4-trifluorophenylaminocarbonyl, 4-heptyloxyphenylaminocarbonyl, 4-dimethylaminophenylaminocarbonyl, 2-(difluoromethoxy)phenylaminocarbonyl, 4-(difluoromethoxy)phenylaminocarbonyl, 3-(trifluoromethylthio)-phenylaminocarbonyl, 2-methylbenzylaminocarbonyl, 3-methylbenzylaminocarbonyl, 4-methylbenzylaminocarbonyl, 2-chlorobenzylaminocarbonyl, 4-fluorobenzylaminocarbonyl, 3,4-dichlorobenzylaminocarbonyl, 4-methoxybenzylaminocarbonyl, 2,6-difluorobenzoylaminocarbonyl, 4-fluorobenzoylaminocarbonyl, 2-fluoro-3-(trifluoromethyl)-phenylaminocarbonyl, 2-fluoro-5-(trifluoromethyl)-phenylaminocarbonyl, 2-fluoro-6-(trifluoromethyl)-phenylaminocarbonyl, 4-fluoro-2-(trifluoromethyl)-phenylaminocarbonyl, 4-fluoro-3-(trifluoromethyl)-phenylaminocarbonyl, 2-cyanophenylaminocarbonyl, 3-cyclopentoxy-4-methoxy-phenylaminocarbonyl, 2-t-butylphenylaminocarbonyl, 4-n-butyl-2-methylphenylaminocarbonyl, 2,6-dibromo-4-isopropylphenylaminocarbonyl and 3-pyridylaminocarbonyl; and $R_{16}$ is selected from the group consisting of cyclopentyl, heptyl, 4-fluorobenzyl, 3-imidazolopropyl, 3-chlorobenzyl, 3-(N-methyl-N-(3-amonopropyl)amino)propyl, 3,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(n-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, L-1-(ethoxycarbonyl)ethyl, 4-aminocyclohexyl, 3,3-dimethylbutyl and methoxycarbonylmethyl.

12. A single triazole compound of claim 1, wherein:

$R_1$ combined with $R_2$ is selected from the group consisting of 4-hydroxyphenyl, 3-chloro-4-hydroxyphenyl, 3-methoxy-4-hydroxyphenyl and 3-hydroxyphenyl;

$R_3$ is selected from the group consisting of 4-methylphenyl, phenyl, 4-chlorophenyl, 3-nitrophenyl and 4-pyridino;

$R_4$ is selected from the group consisting of ethylene, hexamethylene, 2-methylpropylene, -4-$(CH_2CH_2O)C_6H_4CH_2$— and -4-$(CH_2CH_2N(CH_2CH_3))C_6H_4CH_2$—; and $R_5$ is —$NR_{15}R_{16}$, wherein $R_{15}$ is selected from the group consisting of methyl, ethyl, benzyl, butyl, transcinnamyl, cyclohexyl, cyclopropyl, 2,2-diphenylethyl, hydrocinnamyl, isobutyl, isopentyl, 1,3,5-trimethylbenzyl, n-octyl, phenethyl, propyl, 2,2,2-trimethylethyl, n-pentyl, 1,2,3,6-tetrahydrobenzyl, 1,4-benzodioxan-6-methyl, 1-methyl-2-pyrrolemethyl, 1-methylindole-3-methyl, 1-naphthyl, 10-chloro-9-anthryl, 2,3,4-trichlorobenzyl, 2,3,5-trichlorobenzyl, 2,3-(methylenedioxy)benzyl, 2,3-difluorobenzyl, 2,4,5-trimethoxybenzyl, 2,4-dichlorobenzyl, 3,5-difluorobenzyl, 2,5-dimethylbenzyl, 2,6-difluorobenzyl, 2,6-dimethoxybenzyl, 2-bromobenzyl, 2-chloro-6-fluorobenzyl, 2-cyanobenzyl, 2-ethylbutyryl, 2-fluorobenzyl, 2-furyl, 2-methoxy-1-naphthyl, 2-methoxybenzyl, o-anisyl, 2-naphthyl, 2-pyridinemethyl, 2-quinolinemethyl, 2-thiophenemethyl, 3,3-dimethylbutyl, 3,4-(methylenedioxy)benzyl, 3,5,5-trimethylhexyl, 3,5-bis(trifluoromethyl)benzyl, 3,5-dibenzyloxybenzyl, 3,5-dichlorobenzyl, 3,5-dimethoxybenzyl, 3-(trifluoromethyl)benzyl, 3-fluoro-4-methoxybenzyl, 3-fluoro-p-anisyl, 3-fluorobenzyl, 3-furyl, 3-methoxybenzyl, m-anisyl, 3-methyl-4-methoxybenzyl, 2-methylbenzyl, 3-methylbenzyl, m-toluyl, 3-phenylbutyl, 3-pyridinemethyl, 3-quinolinemethyl, 3-thiophenemethyl, 4-(methylthio)benzyl, 4-(trifluoromethyl)benzyl, 4-acetamidobenzyl, 4-methoxybenzyl, 4-benzyloxybenzyl, 4-biphenylmethyl, 4-cyanobenzyl, 4-fluorobenzyl, 4-isopropylbenzyl, 4-methoxy-1-naphthyl, 2,4-dimethoxy-3-methylbenzyl, 4-methylbenzyl, p-toluyl, 4-propoxybenzyl, 4-pyridinemethyl, 4-quinolinemethyl, 5-methyl-2-thiophenemethyl, 5-methyl-2-furyl, 6-methyl-2-pyridinemethyl, pyrrole-2-methyl, 2,4-dimethoxybenzyl, 2,3,4-trimethoxybenzyl, 2,2-dimethyl-4-pentenyl, 3-methoxy-2-nitrobenzyl, 2,5-dimethoxybenzyl, 2-(4-chlorophenylthio)benzyl, 2-methylbutyl, 2-methylpentyl, 2-chlorobenzyl, 2-(trifluoromethyl)benzyl, 2-benzyloxy-3-methoxy-benzyl, 2-phenylpropyl, 3,4,5-trimethoxybenzyl, 3-(methylthio)propyl, 3-chloro-4-fluorobenzyl, 3-chlorobenzyl, 3-methoxy-4,5-methylenedioxybenzyl, 3-methyl-2-butenyl, 4-(diethylamino)benzyl, 4-(trifluoromethoxy)benzyl, 4-acetoxybenzyl, 4-chlorobenzyl, 4-pyrrolidinobenzyl, 5-methylbenzo-b-thiophene-2-methyl, indole-3-methyl, 2-fluoro-3-(trifluoromethyl)benzyl, 2-thiazolemethyl, 4,5-dimethyl-2-furyl, 4-t-butylbenzyl, phenanthrene-9-methyl, 5-(4-chlorophenyl)furfuryl, 3-bromo-4-methoxybenzyl, 5-ethyl-2-furyl, 5-chloro-2-thiophenemethyl, 4-ethylbenzyl, 2,4-diethoxy-m-toluyl, 3-methyl-2-thiophenemethyl, 4-ethoxybenzyl, 2,6-dimethyl-5-heptenyl, 2-chloro-3,4-dimethoxybenzyl, 3,4-diethoxybenzyl, 4-chloro-3-fluorobenzyl, 3-methyl-p-anisyl and 3-methylbutyl; and $R_{16}$ is selected from the group consisting of cyclopentyl, heptyl, 4-fluorobenzyl, 3-imidazolopropyl, 3-chlorobenzyl, 3-(N-methyl-N-(3-aminopropyl)amino)propyl, 3,6-dioxa-8-amino-octyl, 2-trifluoromethylbenzyl, cyclopropyl, 2-thiophenemethyl, 1-indanyl, 4-(aminosulphonyl)phenethyl, 3-ethoxypropyl, 3-(methylthio)propyl, 3-butoxypropyl, 3-(2-oxopyrrolidino)propyl, 2(N-(3-methylphenyl)-ethylamino)ethyl, β-methylphenethyl, 3,5-dimethoxybenzyl, 3-fluoro-5-(trifluoromethyl)benzyl, 1,2-diphenyl-2-aminoethyl, benzyloxycarbonylmethyl, dehydroabietyl, 2-methylcyclohexyl, 4-bromophenethyl, isobutyl, 2-(1-ethyl-pyrrolidinyl)methyl, 3-methoxyphenethyl, 1,4-piperazino-bispropyl, L-1-(ethoxycarbonyl)ethyl, 4-aminocyclohexyl, 3,3-dimethylbutyl and methoxycarbonylmethyl.

\* \* \* \* \*